United States Patent
Russo et al.

(10) Patent No.: US 9,717,801 B2
(45) Date of Patent: Aug. 1, 2017

(54) GLYCOGEN-BASED CATIONIC POLYMERS

(71) Applicant: AZIENDE CHIMICHE RIUNITE ANGELINI FRANCESCO A.C.R.A.F. S.P.A., Rome (IT)

(72) Inventors: Vincenzo Russo, Rome (IT); Elisa Liberati, Rome (IT); Nicola Cazzolla, Albano Laziale (IT)

(73) Assignee: AZIENDE CHIMICHE RIUNITE ANGELINI FRANCESCO A.C.R.A.F. S.p.A., Rome (IT)

( * ) Notice: Subject to any disclaimer, the term of this patent is extended or adjusted under 35 U.S.C. 154(b) by 206 days.

(21) Appl. No.: 14/376,299

(22) PCT Filed: Feb. 21, 2013

(86) PCT No.: PCT/EP2013/053422
§ 371 (c)(1),
(2) Date: Aug. 1, 2014

(87) PCT Pub. No.: WO2013/135471
PCT Pub. Date: Sep. 19, 2013

(65) Prior Publication Data
US 2014/0378532 A1    Dec. 25, 2014

(30) Foreign Application Priority Data
Mar. 15, 2012 (EP) .................................... 12159710

(51) Int. Cl.
| | |
|---|---|
| A61K 47/46 | (2006.01) |
| A61K 47/48 | (2006.01) |
| C08B 37/00 | (2006.01) |
| A61K 31/716 | (2006.01) |
| A61K 31/713 | (2006.01) |
| C08B 37/18 | (2006.01) |

(52) U.S. Cl.
CPC ........ *A61K 47/4823* (2013.01); *A61K 31/713* (2013.01); *A61K 31/716* (2013.01); *C08B 37/0009* (2013.01); *C08B 37/18* (2013.01); *A61K 2201/324* (2013.01); *A61K 2201/326* (2013.01)

(58) Field of Classification Search
None
See application file for complete search history.

(56) References Cited

U.S. PATENT DOCUMENTS

| | | |
|---|---|---|
| 7,144,713 B1 | 12/2006 | McCormick |
| 2007/0178601 A1 | 8/2007 | McCormick |

FOREIGN PATENT DOCUMENTS

| | | |
|---|---|---|
| EP | 2 275 085 | 1/2011 |
| JP | 2011-504457 A | 2/2011 |
| WO | 90 09780 | 9/1990 |
| WO | 94 03502 | 2/1994 |
| WO | 97 25067 | 7/1997 |
| WO | 02 100435 | 12/2002 |
| WO | 03 063827 | 8/2003 |
| WO | 03 078576 | 9/2003 |
| WO | 1 738 769 | 1/2007 |
| WO | 2010128601 A1 | 11/2010 |

OTHER PUBLICATIONS

Jo, J. I., Ikai, T., Okazaki, A., Yamamoto, M., Hirano, Y., & Tabata, Y. (2007). Expression profile of plasmid DNA by spermine derivatives of pullulan with different extents of spermine introduced. Journal of Controlled Release, 118(3), 389-398.*
Chapter 21: Glycogen Metabolism in Biochemistry. 5th edition. Berg JM, Tymoczko JL, Stryer L., Eds. New York: W H Freeman; 2002.*
Bertoldo, M., Zampano, G., Suffner, L., Liberati, E., & Ciardelli, F. (2013). Oxidation of glycogen "molecular nanoparticles" by periodate. Polymer Chemistry, 4(3), 653-661.*
Pal et al., "Synthesis, characterization and flocculation characteristics of cationic glycogen: A novel polymeric flocculant", Colloids and Surfaces A: Physicochem Eng. Aspects, vol. 289, No. 1-3, pp. 193-199, (2006) XP 027995507.
Gubensek et al., "Potentiometric Titration Studies of Diethylaminoethyl Dextran Base", Journal of Macromolecular Science, Part A—Chemistry, pp. 1045-1054, (1968).
Behr, "The Proton Sponge: a Trick to Enter Cells the Viruses did Not Exploit", ILMAC 96: 1st Swiss Cost Chemistry Symposium, vol. 10, pp. 34-64, (1997).
Eliyahu et al., "Polymers for DNS Delivery", Molecules, pp. 34-64, (2005).
Boussif et al., "A versatile vector for gene and oligonucleotide transfer into cells in culture and in vivo: Polyethylenimine", Proc. Natl. Acad. Sci. USA, vol. 92, pp. 7297-7301, (1995).
Waite et al., "Acetylation of PAMAM dendrimers for cellular delivery of siRNA", BMC Biotechnology, (2009).
Snell et al., "Colorimetric Methods of Analysis", vol. III, p. 204, (1954).
International Search Report Issued Mar. 25, 2013 in PCT/EP13/053422 filed Feb. 21, 2013.
Office Action dated Feb. 28, 2017 issued in corresponding Japanese patent application No. 2014-561347 (with English translation).

* cited by examiner

*Primary Examiner* — Shaojia Anna Jiang
*Assistant Examiner* — Dale R Miller
(74) *Attorney, Agent, or Firm* — Oblon, McClelland, Maier & Neustadt, L.L.P.

(57) ABSTRACT

The present invention relates to glycogen-based cationic polymers, to complexes of the said cationic polymers with anionic compounds, to pharmaceutical compositions comprising the said complexes, and to the use of the said complexes for delivering or transfecting the said anionic compounds to a specific pharmacological target, such as, for instance an organ, a tissue or a cell.

17 Claims, 5 Drawing Sheets

GLYCOGEN-BASED CATIONIC POLYMERS

CROSS REFERENCE TO RELATED APPLICATIONS

The present application is a 35 U.S.C. §371 national stage patent application of International patent application PCT/EP2013/053422, filed on Feb. 21, 2013, published as WO/2013/135471 on Sep. 19, 2013, the text of which is incorporated by reference, and claims the benefit of the filing date of European application no. 12159710.8, filed on Mar. 15, 2012, the text of which is also incorporated by reference.

FIELD OF THE INVENTION

The present invention relates to glycogen-based cationic polymers, to complexes comprising the said polymers and at least one anionic compound, and to the use of the said complexes for delivering anionic compounds.

In particular, glycogen-based cationic polymers are useful as non-viral vectors, for the transfection of nucleic acids.

PRIOR ART

In order to reduce the side effects of active principles and to maximize their therapeutic efficacy, controlled-release systems were developed in which the pharmaceutical form controls the phase of release of the active principle, and also systems capable of delivering and directing the active principle to a specific pharmacological target.

In particular, the delivering and directing systems must interact with the active principles in such a way that the complex obtained is stable during storage and administration, but releases the active principle to the correct pharmacological target.

Typically, the interactions that are formed between the delivering system and the active principle are non-covalent, for example electrostatic, ionic or van der Waals interactions, hydrogen bonding and the like.

The problem of developing delivering and directing systems was addressed partly for active principles of low molecular weight, and partly for polymers and molecules of high molecular weight, for instance nucleic acids.

In particular, the voluntary process of insertion of nucleic acid sequences and/or genetic constructs into target cells, for the purpose of compensating for the absence of a gene, overexpressing a gene, silencing the expression of a gene or introducing new functions into the said cell is indicated, in the field of gene therapy, by the term "transfection".

This process appears to be promising both in the treatment of genetic diseases, and in the development of strategies for treating and preventing chronic diseases.

However, when administered in vivo in native form, nucleic acids, much like other polyanionic substances, are rapidly degraded by cationic enzymes (for example nucleases and proteases) and are sparingly absorbed by cells.

The gene vectors that have been studied and developed hitherto include viral systems (retroviruses, adenoviruses, etc.) and non-viral systems (liposomes, polymers, peptides, etc.).

It is known that viral vectors have higher transfection efficiency than non-viral systems. However, the use of viral vectors in vivo is limited by numerous drawbacks, for instance the risk of replication, the possibility of inducing immune reactions, the fact that only subdivided cells are available as targets, the low charge capacity of large-sized genes or the random insertion of DNA fragments.

It is known in the art that the use of gene therapies based on non-viral vectors comprises numerous advantages, among which are the relative safety and the low preparation costs.

Non-viral gene vectors, for instance cationic polymers, liposomes and synthetic vectors, have been widely studied as an alternative to the use of viral vectors.

N,N-Diethylaminoethyl-dextran (DEAE-dextran) was one of the first chemical derivatives of a natural polymer to be used for the controlled release of active principles (for example for controlled release into mucosae as described, for example, in WO 90/09780) and, subsequently, as a transfection agent (as described, for example, in EP 1 738 769).

DEAE-dextran is a polycationic polymer, obtained by reacting N,N-diethylaminoethyl chloride and dextran, which is a linear polymer in which the glucose units are bonded via α-1,6 bonds, with little branching, in which the glucose monomers are bonded via α-1,4 bonds (the numbering is shown in the formula below).

DEAE-Dextran, represented by the following structural formula, has two substituents comprising nitrogenous residues, in which the nitrogen atoms have different physico-chemical characteristics from each other:

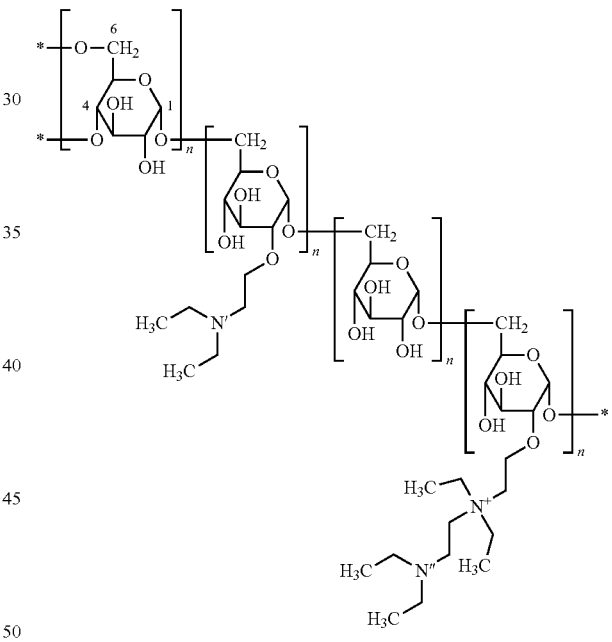

The first substituent comprises a tertiary amine function (indicated as N') with a $pK_a$ of about 9.5, which, at physiological pH, is in ionized form. The second substituent, known as the "tandem", comprises a quaternary ammonium group ($N^+$), which has a permanent positive charge and influences the acidity of the second tertiary amine function (indicated as N") which has a $pK_a$ of about 5.7 and then, at physiological pH, is in non-ionized form (F. Gubensek, Journal of Macromolecular Science Part A—Chemistry—2 (5) 1968, 1045-1054).

It is known, however, that the positive charges of DEAE-dextran in vivo interact with anionic biological structures, other than nucleic acids, resulting in toxicity phenomena.

In general, the mechanism of formation of complexes between cationic polymers and nucleic acids and the subsequent delivering may be summarized as follows.

The genetic material is complexed by cationic polymers via weak interactions, for example electrostatic interactions. The formation of this complex protects the nucleic acid from nuclease degradation and enables the nucleic acid to be delivered into the cell since the positive charges present on the surface of the complex interact with the cell membrane, stimulating endocytosis of the complex, via the formation of endosomes.

The interior of the endosomes has a pH of about 4.5-5, which is much more acidic than the pH of the cytoplasmic medium, which is at about 7.3. This difference in pH is maintained by an ATP-dependent proton pump present on the endosomal membrane, which pushes H$^+$ ions from the cytosol into the endosome. The acidic pH promotes the activity of the lysosomal nucleases, which are the enzymes responsible for the degradation of nucleic acids by hydrolysis of the phosphodiester bonds between nucleotide subunits.

Polymers with buffer capacity inhibit the activity of the lysosomal nucleases and, at the same time, alter the osmolarity of the endosomes.

In point of fact, while the polymers are sequestering H$^+$ ions, other H$^+$ ions are required by the cytosol, at the same time as or ions to maintain the electrical neutrality of the endosome. However, the demand for H$^+$ and Cl$^-$ ions results in an increase in the concentration of ions inside the endosome, with a consequent increase in the osmolarity of the endosome relative to the cytosol. The increase in osmolarity demands water from the cytosol. Consequently, the endosome swells until it ruptures, releasing the polymer-nucleic acid complex into the cytoplasm.

This mechanism, known as the "proton sponge mechanism", was described, inter alia, by J-P. Behr in "*The proton sponge: a trick to enter cells the viruses did not exploit*" (Chimia, 1997, 51, 34-36) in relation to polyethyleneimine (PEI) polymers and, more generally, by H. Eliyahu et al. in "*Polymers for DNA delivery*" (*Molecules*, 2005, 10, 34-64).

Polyethyleneimines (PEI) are linear or branched cationic polymers characterized by highly efficient release of oligonucleotides and plasmids into cells, in vitro, as described, for example, by O. Boussif et al. in "*A versatile vector for gene and oligonucleotide transfer into cells in culture and in vivo: Polyethylenimine*" (Proc. Natl. Acad. Sci. USA, 1995, Vol. 92, 7297-7301) and in international patent application WO 02/100435. PEIs are described as polymers with a high charge density which protect nucleic acids against degradation by nucleases. It is thought that the high buffer capacity of PEI protects the nucleic acid against degradation in the endosomes during the phase of cell uptake, by inducing osmotic swelling ("proton sponge" mechanism) of the endosome, which enables the release of the vector-nucleic acid complex into the cytoplasm.

Another polymer that has been widely studied as a transfection agent is poly(L-lysine) (PLL), which has been described, for example, in international patent application WO 03/063827, which is characterized by primary amine groups that are ionized at physiological pH, which interact with the phosphate groups of nucleic acids, which are negatively charged. However, the toxicity and the transfection efficacy of PLL are directly proportional to their molecular weight: as the molecular weight of the polymer increases, increased transfection efficacy is observed, on one hand, and increased cytotoxicity, on the other hand. In addition, the main chain of PLL is barely degraded under physiological conditions, and its accumulation may lead to toxic consequences in the long run.

As for the majority of cationic polymers, complexes of PLL with nucleic acids also have physicochemical drawbacks. For example, the preparation processes offer little capacity for size control, and this may lead to the presence of large particles with limited diffusion capacity and/or the possibility of precipitation during the phase of formulation or administration. In addition, it appears that the acid-base characteristics of PLL do not make it possible to obtain high transfection efficacy, probably because of the limited capacity for release of the nucleic acid into the cytoplasmic medium.

Other cationic polymers, both natural and synthetic, have been described in the prior art as transfection agents for nucleic acids.

For example, international patent application WO 03/078576 describes chitosan as a transfection agent for nucleic acids.

Chitosan is a natural linear polymer, composed of D-glucosamine and N-acetyl-D-glucosamine units distributed randomly in the polymer, linked via β-1,4 bonds and comprising an amine group with a pK$_a$ of about 6.5.

As transfection agents for nucleic acids, extensive studies have also been performed on dendrimers comprising positively ionizable groups, for example of poly(amidoamine) (PAMAM) structure, macromolecules of linear structure; methacrylic polymers (such as N,N-di methylaminoethyl methacrylate, DMAEMA), poly(ethyleneimine) (PEI), and derivatives of these polymers with solubilizing, functional or directing groups, for example polymeric structures containing poly(ethylene glycol) (PEG).

The linear poly(amidoamines) (PAMAM) described, for example, in international patent application WO 97/25067 are water-soluble polymers that allow the formation of soluble and/or dispersible complexes. Preferably, the pK$_a$ value of the cationic groups of these polymers should be maintained between 7 and 8, since it is known that lower pK$_a$ values reduce the capacity for charging with nucleic acids. Also, the release of complexes formed from dendrimers based on PAMAM and nucleic acids by endosomes involves the "proton-sponge" effect. Specifically, C. L. Waite et al. in "*Acetylation of PAMAM dendrimers for cellular delivery of siRNA*" (BMC Biotechnology, 2009, 9:38) describe that the partial acetylation of the primary amine residues reduces both the buffer capacity of PAMAM-based dendrimers and the release of siRNA.

Cationic polymers have been developed also for applications other than transfection agents for nucleic acids.

For example, in paragraph 2.2 of the article to Pal S et al. (Colloids and Surfaces A: Physicochem. Eng. Aspects 289, 2006, pages 193-199) it is disclosed how glycogen has been cationised by incorporating a cationic monomer N-(3-chloro-2-hydroxypropyl)-trimethyl ammonium chloride onto the backbone of polysaccharide glycogen. Said cationic polymer was found to be effective as flocculation agent in iron ore suspensions.

It is known that an ideal transfection agent should ensure a high transfection capacity, without it being necessary to manipulate the physiological target; it should not be toxic at the effective dose and should be biodegradable, so as to avoid any long-term side effects.

In addition, should the transfection agent be a polymer, it should form particles smaller than a micrometer (i.e. less than 10$^{-6}$ m) and should preferably form nanoparticles, since it is known that the size can limit both the diffusion capacity of the complex in the extracellular medium, and the endocytosis/phagocytosis efficiency in cells.

Finally, the polymeric structure should comprise amine groups and/or nitrogen atoms characterized by various pK$_a$ values. In fact, amine groups with pK$_a$ values higher than the physiological pH value facilitate the complexation of nucleic acid at physiological pH; amine groups with pK$_a$ values of about the endosomal pH value activate the "proton-sponge" mechanism and ensure the release of the polymer-nucleic acid complex into the cytoplasm; finally, quaternary ammonium groups ensure complexation and release from the endosome independently of the pH value.

SUMMARY OF THE INVENTION

The Applicant has addressed the problem of developing novel polymers that can be used both for delivering low molecular weight active principles and as non-viral vectors for nucleic acids, and which can overcome the drawbacks of the materials known in the prior art.

Surprisingly, the Applicant has now found that glycogen can be modified so as to obtain novel cationic derivatives.

Advantageously, the said novel cationic derivatives of glycogen are characterized by low cytotoxicity.

The Applicant believes that this is due mainly to two reasons. Firstly, glycogen is a biocompatible polymer, which is a product of the metabolism and storage of sugars in all animal bodies, where it is continuously produced and degraded. In addition, the Applicant believes that the numerous branches in glycogen give the structure a stable spherical conformation that is capable of selectively reducing the access to cationic charges: soluble molecules can diffuse inside the polymer structure and become complexed by the cationic sites, whereas, in contrast, interactions with more complex structures would not be permitted anymore for steric reasons. This spherical conformation would make it possible to reduce the toxicity of the cationic charges, which typically damage cell membranes.

The Applicant has found that the novel cationic derivatives of glycogen conserve the biocompatibility characteristics of the natural polymer from which they are derived.

The Applicant has also found that these novel cationic derivatives of glycogen are capable of forming complexes with anionic compounds that have sizes and molecular weights within a wide range.

Advantageously, the said complexes are of nanometric size and do not show any aggregation when they are in solution, even at high concentrations.

The Applicant has found that the novel cationic derivatives of glycogen can deliver anionic compounds to specific physiological targets (for example organs, tissues and cells).

The Applicant has also found that the cationic derivatives of glycogen according to the present invention are capable of penetrating into cells.

Consequently, the said novel cationic derivatives of glycogen can be used for delivering anionic compounds into cells.

Finally, the Applicant has found that the cationic derivatives of glycogen according to the present invention can be used as stabilizers, in the conservation of proteins and enzymes, and as coadjuvants in the production of vaccines.

Advantageously, the novel cationic derivatives of glycogen comprise substituents bearing amine groups characterized by $pK_a$ values that are different from each other, so as to facilitate both the complexation of anionic compounds and the release of the polymer-anionic compound complexes from the endosome to the cytoplasm.

Advantageously, the novel cationic derivatives of glycogen according to the present invention have low viscosity and, consequently, can be formulated in pharmaceutical compositions for injectable use.

In a first aspect, the present invention thus relates to novel cationic polymers based on modified glycogen, in particular the present invention relates to cationic polymers based on glycogen, which comprise at least one repeating unit chosen from the group consisting of:

(a)

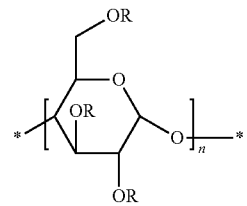

(a)

in which the groups R, which may be identical or different, are a hydrogen atom; a carboxymethyl group, optionally in salt form with a pharmaceutically acceptable organic or inorganic base; or a group containing nitrogen chosen from: $NH_2$—$(C_1-C_6)$alkyl, [N,N-di$(C_1-C_6)$alkylamino]-$(C_1-C_6)$alkyl, $NH_2$—{[$(C_1-C_6)$alkyl]-di$(C_1-C_6)$alkylammonio}-$(C_1-C_6)$alkyl, {[N,N-di$(C_1-C_6)$alkylamino]-$(C_1-C_6)$alkyl-di$(C_1-C_6)$alkylammonio}-$(C_1-C_6)$alkyl, $NH_2$—[$(C_1-C_6)$alkylamino]-$(C_1-C_6)$alkyl, {[N,N-di$(C_1-C_6)$alkylamino]-$(C_1-C_6)$alkylamino}-$(C_1-C_6)$alkyl, [tri$(C_1-C_6)$alkylammonio]-$(C_1-C_6)$alkyl, azocyclyl-$(C_1-C_6)$alkyl, in which the chains $(C_1-C_6)$alkyl, which may be identical or different, are optionally substituted with one or more hydroxyl groups; and n is an integer greater than or equal to 1; and (b)

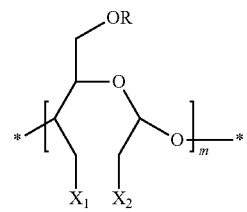

(b)

in which $R_1$ is chosen from a hydrogen atom; a carboxymethyl group, optionally in salt form with a pharmaceutically acceptable organic or inorganic base; or a group containing nitrogen chosen from: $NH_2$—$(C_1-C_6)$alkyl, [N,N-di$(C_1-C_6)$alkylamino]-$(C_1-C_6)$alkyl, $NH_2$—[$(C_1-C_6)$alkyl-di$(C_1-C_6)$alkylammonio]-$(C_1-C_6)$alkyl, {[N,N-di$(C_1-C_6)$alkylamino]-$(C_1-C_6)$alkyl-di$(C_1-C_6)$alkylammonio}-$(C_1-C_6)$alkyl, $NH_2$—[$(C_1-C_6)$alkylamino]-$(C_1-C_6)$alkyl, {[N,N-di$(C_1-C_6)$alkylamino]-$(C_1-C_6)$alkylamino}-$(C_1-C_6)$alkyl, [tri$(C_1-C_6)$alkylammonio]-$(C_1-C_6)$alkyl, in which the chains $(C_1-C_6)$alkyl, which may be identical or different, are optionally substituted with one or more hydroxyl groups;

$X_1$ and $X_2$, which may be identical or different, are a group —OH or a group containing nitrogen —$NHR_2$, in which $R_2$ is chosen from: hydrogen atom, $(C_1-C_6)$alkyl, and H—[NH—$(C_1-C_6)$alkyl]$_p$-, where p is an integer greater than or equal to 1 and the groups $(C_1-C_6)$alkyl may be identical or different; and m is an integer greater than or equal to 1;

on condition that at least one from among R, $R_1$, $X_1$ and $X_2$ is a group containing nitrogen as defined, respectively, for each of R, $R_1$, $X_1$ and $X_2$ and provided that said glycogen-based cationic polymer is different from the product obtained by the reaction of glycogen with N-(3-chloro-2-hydroxypropyl)-trimethyl ammonium chloride.

The abovementioned expression "on condition that at least one from among R, $R_1$, $X_1$ and $X_2$ is a group containing nitrogen as defined, respectively, for each of R, $R_1$, $X_1$ and $X_2$" means that, in the case where R is a group containing nitrogen, this group is as defined in R, in the case where $R_1$ is a group containing nitrogen, this group is as defined in $R_1$, in the case where $X_1$ is a group containing nitrogen, this group is as defined in $X_1$, and in the case where $X_2$ is a group containing nitrogen, this group is as defined in $X_2$.

In a second aspect, the present invention relates to a complex between a glycogen-based cationic polymer and an anionic compound.

According to a preferred embodiment, the said anionic compound is an active principle. Advantageously, the said anionic compound is a nucleic acid.

In a third aspect, the present invention relates to a pharmaceutical composition comprising a complex between a glycogen-based cationic polymer and an anionic compound, and at least one pharmaceutically acceptable excipient.

In a fourth aspect, the present invention relates to the use of a complex between a glycogen-based cationic polymer and an anionic compound, for delivering or transfecting the said anionic compound into a specific pharmacological target, for example an organ, a tissue or a cell.

According to one preferred embodiment, the said anionic compound is an active principle. Advantageously, the said anionic compound is a nucleic acid.

BRIEF DESCRIPTION OF THE FIGURES

FIG. 1 represents an agarose gel on which were seeded complexes obtained between polymer 3 according to the invention and siRNA at various concentrations (from 0.5% to 8% by weight). Polymer 3 free of nucleic acid (0%) was used as comparative to check that the cationic polymer according to the invention does not interfere with the detection of the spot relative to siRNA.

FIG. 2 represents an agarose gel on which were seeded:
complexes obtained between polymer 3 according to the invention and siRNA at concentrations from 10% to 20% by weight;
polymer 3 free of nucleic acid (0%) as comparative to check that the cationic polymer according to the invention does not interfere with the detection of the spot relative to siRNA; and
polymer 50 (unmodified Polglumyt™ glycogen) as comparative to check that glycogen, not modified according to the present invention, is incapable of complexing nucleic acids.

FIG. 3 represents an agarose gel on which were seeded complexes obtained between polymer 3 according to the invention and siRNA at various concentrations (from 30% to 800% by weight).

FIG. 4 represents an agarose gel on which were seeded complexes obtained between polymers 1, 2 and 6 according to the invention and siRNA at concentrations of 5% and 20% by weight relative to the total weight of each polymer.

FIG. 5 represents an agarose gel on which were seeded complexes obtained between polymers 10, 14 and 15 according to the invention and siRNA at concentrations of 5% and 20% by weight relative to the total weight of each polymer.

FIG. 6 represents an agarose gel on which were seeded complexes obtained between polymers 8, 12 and 16 according to the invention and siRNA at concentrations of 5% and 20% by weight relative to the total weight of each polymer.

FIG. 7 represents an agarose gel on which were seeded complexes obtained between polymers 21, 24 and 25 according to the invention and siRNA at concentrations of 5% and 20% by weight relative to the total weight of each polymer.

FIG. 8 represents an agarose gel on which were seeded complexes obtained between polymers 20, 23 and 28 according to the invention and siRNA at concentrations of 5% and 20% by weight relative to the total weight of each polymer.

DETAILED DESCRIPTION OF THE INVENTION

Figure 1:
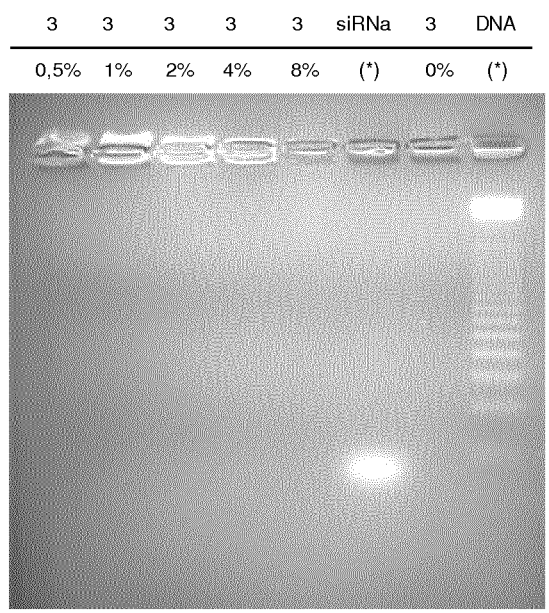
FIGS. 1 to 8 represent eight agarose gels obtained following gel electrophoresis, as described in Example 5. In all the FIGS. 1 to 8, siRNA(*) and DNA(*) markers were seeded to obtain the corresponding bands, used for comparative purposes and to check the functioning of the electrophoresis method.

In the present description and in the claims that follow, the wording "cationic polymer" indicates a polymer with an overall positive charge, at physiological pH.

In the present description and in the claims that follow, the term "glycogen" indicates, in general, a glucose homopolymer characterized by a high degree of branching, in which the glucose monomers are bonded by means of α-(1,4) bonds in the linear chains, while the branches are grafted by means of α-(1,6) bonds, generally, but without limitation, every 7-11 glucose monomers, as shown in the following formula:

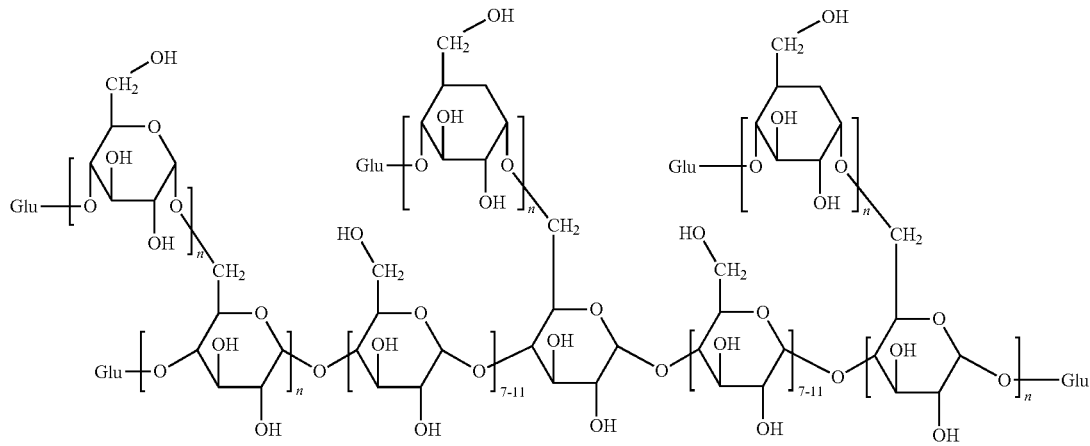

For the purposes of the present description and of the claims that follow, the wording "glycogen-based" is used to indicate that the polymer comprises the glycogen structure described above, which is partly modified to obtain the cationic polymer according to the present invention.

For the purposes of the present description and of the claims that follow, the wording "repeating unit" identifies a monomer that is present at least once in the cationic polymer according to the present invention.

For the purposes of the present description and the claims that follow, the wording "$(C_1-C_6)$alkyl" indicates a linear or branched alkyl group containing from 1 to 6 carbon atoms, for example methyl, ethyl, propyl, isopropyl, n-butyl, isobutyl, sec-butyl, tert-butyl, n-pentyl, sec-pentyl, 3-pentyl, isopentyl, neopentyl, n-hexyl, sec-hexyl or neohexyl.

For the purposes of the present description and of the claims that follow, the term "azocyclyl" indicates a 3- to 7-membered aromatic or aliphatic heterocyclic ring, containing at least one N atom, such as, for instance aziridine, pyrrole, pyrroline, pyrrolidine, pyridine or piperidine. Optionally, the abovementioned heterocyclic ring may comprise at least a second heteroatom chosen from N, O and S, such as, for instance thiazole, oxazine or thiazine.

For the purposes of the present description and of the claims that follow, the term "complex" indicates a product obtained by the interaction of the glycogen-based cationic polymer according to the present invention with at least one anionic compound, via non-covalent interactions (for example electrostatic, ionic or Van der Waals interactions, hydrogen bonding and the like).

For the purposes of the present description and of the claims that follow, the wording "active principle" comprises natural, semi-synthetic or synthetic molecules, which, after administration, are capable of interacting with a biological function of a cell or of a live organism and possibly of modifying the said biological function. The active principles that are useful according to the present invention are thus molecules with an overall negative charge, that is to say anionic molecules, which may be used for the therapy, prophylaxis or diagnosis of a pathological condition. The said anionic molecules may be organic or inorganic. For example, they may be organic anionic molecules and may have a low molecular weight (for example amino acids, sulfamides or vitamins) or a high molecular weight (for example vaccines, or glucosaminoglycans such as heparin).

For the purposes of the present description and of the claims that follow, the term "nucleic acid" indicates nucleotide macromolecules, of natural or synthetic origin, which are double-stranded or single-stranded, and which have an overall negative charge. In particular, this term includes oligonucleotides, RNA (siRNA, dsRNA, ssRNA, shRNA, miRNA, rRNA, hnRNA, mRNA, tRNA, snRNA, pre-mRNA, catalytic RNA, antisense RNA), DNA (cDNA, mtDNA, ssDNA, dsDNA, antisense DNA, plasmid DNA).

For the purposes of the present description and of the claims that follow, the wordings "delivery of an active principle" and "delivering an active principle" indicate the transportation of the active principle complexed to the cationic polymer according to the present invention to a specific physiological target, for example a tissue or an organ.

For the purposes of the present description and of the claims that follow, the terms "transfection" and "transfecting" indicate the introduction of a nucleic acid sequence into a cell, in particular into the cytoplasm and/or the nucleus.

In particular, the present invention relates to a glycogen-based cationic polymer comprising at least one repeating unit chosen from the group consisting of:

(a)

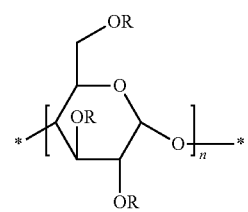

in which the groups R, which may be identical or different, are a hydrogen atom; a carboxymethyl group, optionally in salt form with a pharmaceutically acceptable organic or inorganic base; or a group containing nitrogen chosen from $NH_2-(C_1-C_6)$alkyl, $[N,N-di(C_1-C_6)alkylamino]-(C_1-C_6)$alkyl, $NH_2-[(C_1-C_6)alkyl-di(C_1-C_6)alkylammonio]-(C_1-C_6)$alkyl, $\{[N,N-di(C_1-C_6)alkyl-amino]-(C_1-C_6)alkyl-di(C_1-C_6)alkylammonio\}-(C_1-C_6)$alkyl, $NH_2-[(C_1-C_6)alkylamino]-(C_1-C_6)$alkyl, $[N,N-di(C_1-C_6)alkylamino]-(C_1-C_6)$alkylamino$\}-(C_1-C_6)$alkyl, $[tri(C_1-C_6)alkylammonio]-(C_1-C_6)$alkyl, azocyclyl-$(C_1-C_6)$alkyl, in which the chains $(C_1-C_6)$alkyl, which may be identical or different, are optionally substituted with one or more hydroxyl groups; and n is an integer greater than or equal to 1; and (b)

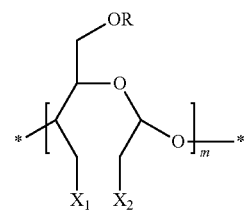

in which $R_1$ is chosen from a hydrogen atom; a carboxymethyl group, optionally in salt form with a pharmaceutically acceptable organic or inorganic base; or a group containing nitrogen chosen from $NH_2-(C_1-C_6)$alkyl, $[N,N-di(C_1-C_6)alkylamino]-(C_1-C_6)$alkyl, $NH_2-[(C_1-C_6)alkyl-di(C_1-C_6)alkylammonio]-(C_1-C_6)$alkyl, $\{[N,N-di(C_1-C_6)alkylamino]-(C_1-C_6)alkyl-di(C_1-C_6)alkylammonio\}-(C_1-C_6)$alkyl, $NH_2-[(C_1-C_6)alkylamino]-(C_1-C_6)$alkyl, $\{[N,N-di(C_1-C_6)alkylamino]-(C_1-C_6)alkylamino\}-(C_1-C_6)$alkyl, $[tri(C_1-C_6)alkylammonio]-(C_1-C_6)$alkyl, in which the chains $(C_1-C_6)$alkyl, which may be identical or different, are optionally substituted with one or more hydroxyl groups;

$X_1$ and $X_2$, which may be identical or different, are a group —OH or a group containing nitrogen —$NHR_2$, in which $R_2$ is chosen from: hydrogen atom, $(C_1-C_6)$alkyl, and H—[NH—$(C_1-C_6)$alkyl]$_p$-, where p is an integer greater than or equal to 1 and the groups $(C_1-C_6)$alkyl may be identical or different; and m is an integer greater than or equal to 1;

on condition that at least one from among R, $R_1$, $X_1$ and $X_2$ is a group containing nitrogen as defined, respectively, for each of R, $R_1$, $X_1$ and $X_2$ and provided that said glycogen-based cationic polymer is different from the product obtained by the reaction of glycogen with N-(3-chloro-2-hydroxypropyl)-trimethyl ammonium chloride, as disclosed, in particular, in paragraph 2.2 of the article to Pal S et al. (Colloids and Surfaces A: Physicochem. Eng. Aspects 289, 2006, pages 193-199).

Preferably, the groups R, which may be identical or different, are a hydrogen atom; a carboxymethyl group, optionally in salt form with a pharmaceutically acceptable organic or inorganic base; or a group containing nitrogen chosen from: [N,N-di($C_1$-$C_3$)alkylamino]-($C_1$-$C_3$)alkyl, {[N,N-di($C_1$-$C_3$)alkylamino]-($C_1$-$C_3$)alkyl-di($C_1$-$C_3$)alkylammonio}-($C_1$-$C_3$)-alkyl, {[N,N-di($C_1$-$C_3$)alkylamino]-($C_1$-$C_3$)alkylamino}-($C_1$-$C_3$)alkyl, or [tri($C_1$-$C_3$)alkylammonio]-($C_1$-$C_3$)alkyl, azocyclyl-($C_1$-$C_3$)alkyl, in which the chains ($C_1$-$C_3$)alkyl, which may be identical or different, are optionally substituted with a hydroxyl group.

Preferably, the heterocyclic ring containing at least one N atom represented by the term "azocyclyl" is a 5- or 6-membered aromatic or aliphatic heterocyclic ring, such as, for instance pyrrole, pyrroline, pyrrolidine, pyridine or piperidine. Advantageously, the said 5- or 6-membered heterocyclic ring comprises at least a second heteroatom chosen from N, O and S and is represented, for example, by diazole, oxazine and thiazine. Preferably, the said heterocyclic ring is aliphatic. Even more preferably, the said heterocyclic ring is morpholine or piperidine.

More preferably, the groups R, which may be identical or different, are a hydrogen atom; a carboxymethyl group, optionally in salt form with a pharmaceutically acceptable organic or inorganic base; or a group containing nitrogen chosen from: N,N-dimethylaminoethyl, N,N-di methylaminopropyl, N,N-diethylaminoethyl, [(N,N-dimethylaminoethyl)dimethylammonio]ethyl, [(N,N-dimethylaminopropyl)dimethylammonio]propyl, [(N,N-diethylamino-ethyl)diethylammonio]-ethyl, [trimethylammonio]-2-hydroxypropyl, piperidyl-N-ethyl or morpholinyl-N-ethyl.

Preferably, $R_1$ is a hydrogen atom; a carboxymethyl group, optionally in salt form with a pharmaceutically acceptable organic or inorganic base; or a group containing nitrogen chosen from: [N,N-di($C_1$-$C_3$)alkylamino]-($C_1$-$C_3$)alkyl], {[N,N-di($C_1$-$C_3$)alkylamino]-($C_1$-$C_3$)alkyl-di($C_1$-$C_3$)alkylammonio}-($C_1$-$C_3$)alkyl, {[N,N-di($C_1$-$C_3$)alkylamino]-($C_1$-$C_3$)alkylamino}-($C_1$-$C_3$)alkyl or [tri($C_1$-$C_3$)alkylammonio]-($C_1$-$C_3$)alkyl, in which the chains ($C_1$-$C_3$) alkyl, which may be identical or different, are optionally substituted with a hydroxyl group.

More preferably, $R_1$ is a hydrogen atom or a carboxymethyl group.

Preferably, $X_1$ and $X_2$, which may be identical or different, are a group —$NHR_2$, in which $R_2$ is a hydrogen atom or H—[NH—($C_1$-$C_4$)alkyl]$_p$-, where p is an integer greater than or equal to 1 and the groups ($C_1$-$C_4$)alkyl may be identical or different.

Preferably, the said group H—[NH—($C_1$-$C_4$)alkyl]$_p$- is a polyethyleneimine, with a molecular weight of from 50 to 3,000 daltons and more preferably with a molecular weight of from 1,000 to 2,300 daltons, spermine ($H_2N(CH_2)_3NH(CH_2)_4NH(CH_2)_3NH_2$), or spermidine ($H_2N(CH_2)_4NH(CH_2)_4NH_2$).

Examples of pharmaceutically acceptable organic bases are tromethamine, lysine, arginine, glycine, alanine, methylamine, dimethylamine, trimethylamine, ethylamine, diethylamine, triethylamine, propylamine, dipropylamine, tripropylamine, ethylenediamine, monoethanolamine, diethanolamine, triethanolamine, guanidine, morpholine, piperidine, pyrrolidine, piperazine, 1-butylpiperidine, 1-ethyl-2-methylpiperidine, N-methylpiperazine, 1,4-dimethylpiperazine, N-benzylphenethylamine, N-methylglucosamine and tris(hydroxymethyl)aminomethane.

Examples of pharmaceutically acceptable inorganic bases are alkali metal or alkaline-earth metal hydroxides or carbonates, such as, for instance sodium hydroxide, potassium hydroxide, calcium hydroxide, sodium carbonate, potassium carbonate and calcium carbonate.

Advantageously, the said repeating units (a) and (b) are arranged randomly in the glycogen chains.

Examples of repeating units (a) and (b) are represented, respectively, in Tables A and B below.

TABLE A

Examples of repeating units (a)

| Substituent position | Substituent | Repeating unit of formula (a) |
|---|---|---|
| 6 | N,N-diethyl-aminoethyl | 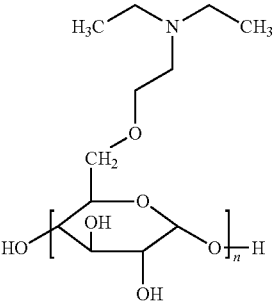 |
| 6 | N,N-dimethyl-aminoethyl | 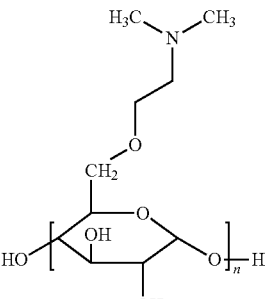 |
| 6 | N,N-dimethyl-aminopropyl | 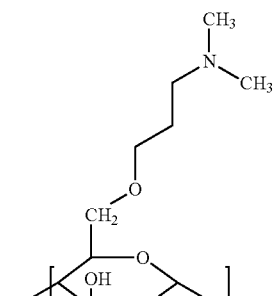 |

TABLE A-continued

Examples of repeating units (a)

| Substituent position | Substituent | Repeating unit of formula (a) |
|---|---|---|
| 6 | [(N,N-diethyl-aminoethyl)-diethyl-ammonio]ethyl | 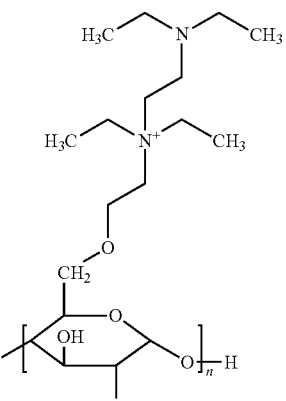 |
| 6 | [(N,N-dimethyl-aminopropyl)-dimethyl-ammonio]propyl | 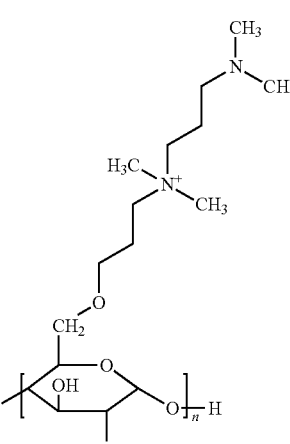 |
| 6 | [(N,N-dimethyl-aminoethyl)-dimethyl-ammonio]ethyl | 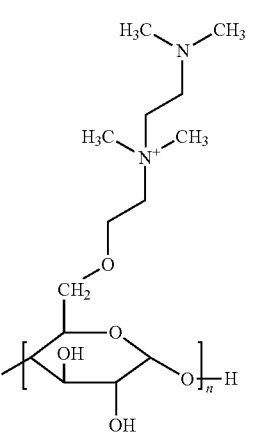 |
| 6 | [trimethyl-ammonio]-2-hydroxypropyl | 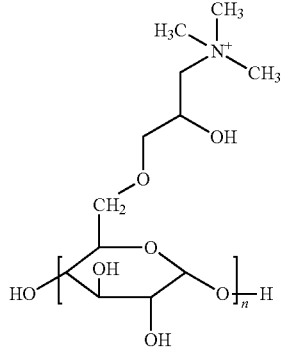 |
| 2 | [trimethyl-ammonio]-2-hydroxypropyl | 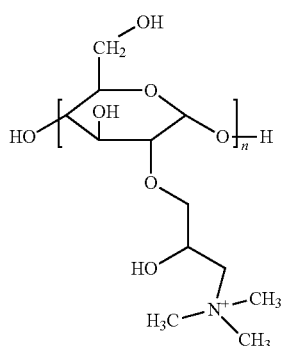 |
| 6<br>2 | [(N,N-dimethyl-aminopropyl)-dimethyl-ammonio]propyl<br>N,N-dimethyl-aminopropyl | 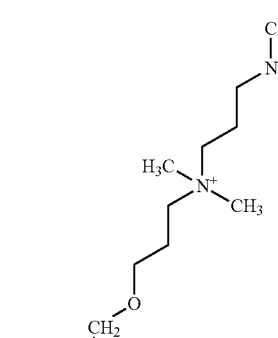 |

TABLE A-continued

Examples of repeating units (a)

| Substituent position | Substituent | Repeating unit of formula (a) |
|---|---|---|
| 6<br>2, 3 | [(N,N-diethyl-aminoethyl)-diethyl-ammonio]ethyl<br>N,N-diethyl-aminoethyl | 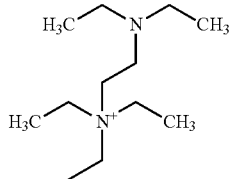 |
| 3 | N,N-dimethyl-aminoethyl | 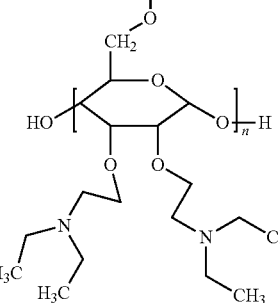 |
| 6<br>3 | N,N-dimethyl-aminoethyl<br>N,N-diethyl-aminoethyl | 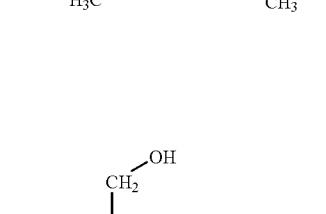 |
| 6 | carboxymethyl | 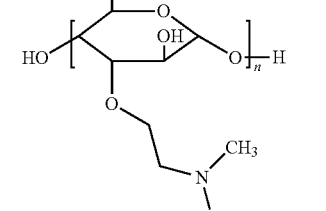 |
| 6 | carboxymethyl sodium salt | 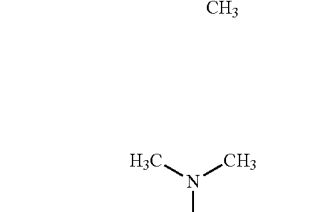 |
| 6<br>3 | trimethyl-ammonio-2-hydroxypropyl<br>N,N-diethyl-aminoethyl | 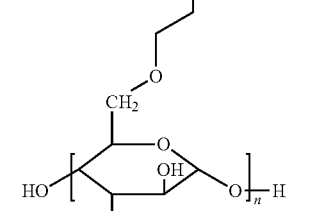 |

TABLE A-continued

Examples of repeating units (a)

| Substituent position | Substituent | Repeating unit of formula (a) |
|---|---|---|
| 6<br>3 | [trimethyl-ammonio]-2-hydroxypropyl<br>[(N,N-diethyl-aminoethyl)-diethyl-ammonio]ethyl | |
| 6<br>2 | N,N-dimethyl-aminopropyl<br>carboxymethyl | |
| 6<br>3 | [(N,N-dimethyl-aminopropyl)-dimethyl-ammonio]propyl<br>carboxymethyl sodium salt | |
| 6<br>2 | carboxymethyl<br>[trimethyl-ammonio]propyl | |
| 2<br>3 | N,N-diethyl-aminoethyl<br>carboxymethyl sodium salt | |
| 6 | N-ethylpiperidyl | |

TABLE A-continued
Examples of repeating units (a)
| Substituent position | Substituent | Repeating unit of formula (a) |
|---|---|---|
| 6 | N-ethyl-morpholinyl | 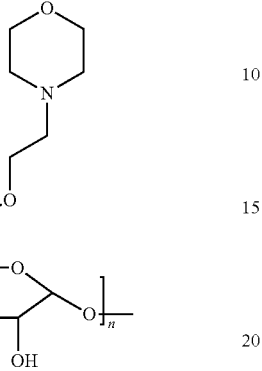 |
TABLE B
Examples of repeating units (b)
| Substituent position | Substituent | Repeating unit of formula (b) |
|---|---|---|
| 2 | Spermine | 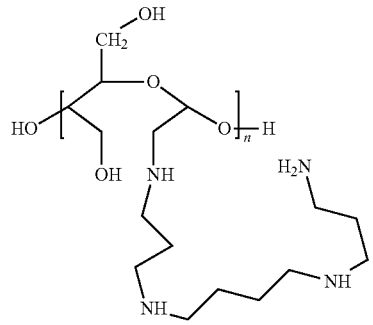 |
| 2, 3 | Spermine | 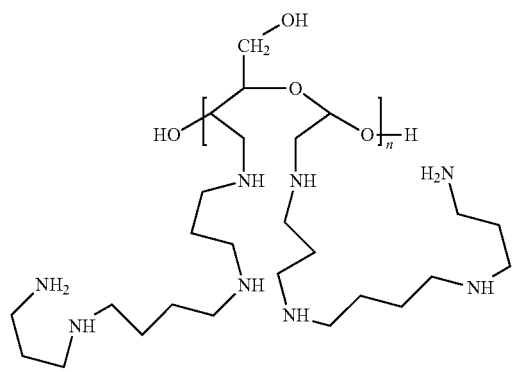 |

TABLE B-continued
| | Examples of repeating units (b) | |
|---|---|---|
| Substituent position | Substituent | Repeating unit of formula (b) |
| 2 | Tetraethylene-pentamine | 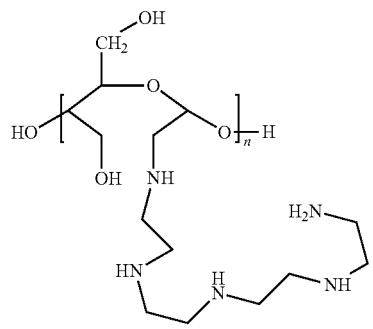 |
| 2, 3 | Tetraethylene-pentamine | 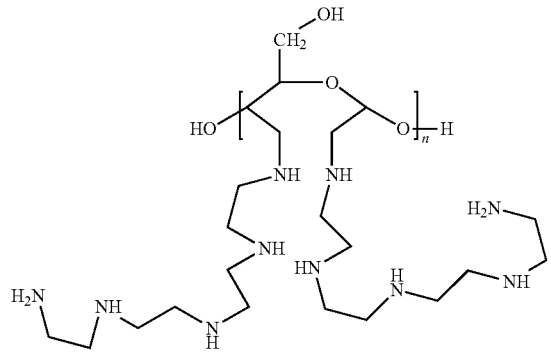 |
| 6<br>2 | Carboxymethyl<br>Tetraethylene-pentamine | 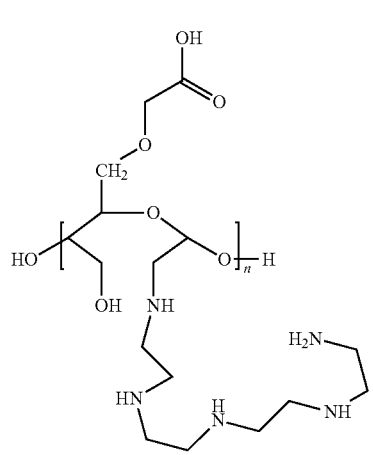 |

TABLE B-continued
Examples of repeating units (b)
| Substituent position | Substituent | Repeating unit of formula (b) |
|---|---|---|
| 6<br>2, 3 | Carboxymethyl<br>Spermine | 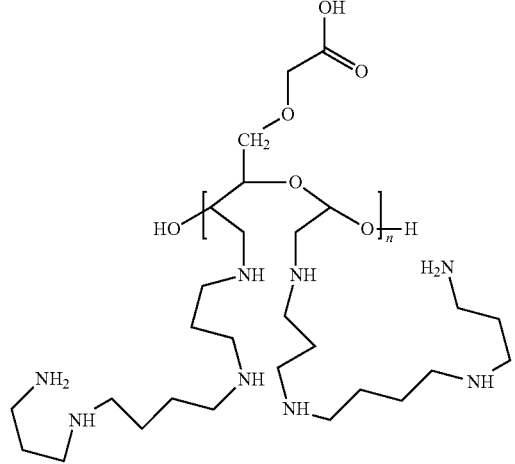 |
| 2 | Polyethylene-imine (MW = 1300 Da) | 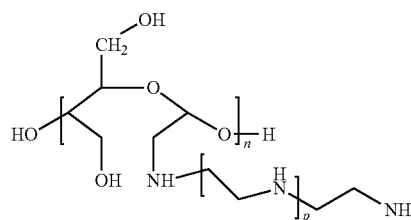 |
| 3 | Polyethylene-imine (MW = 2000 Da) | 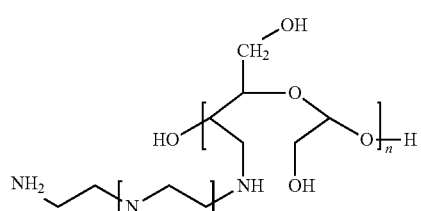 |
| 2<br>6 | Polyethylene-imine<br>Carboxymethyl | 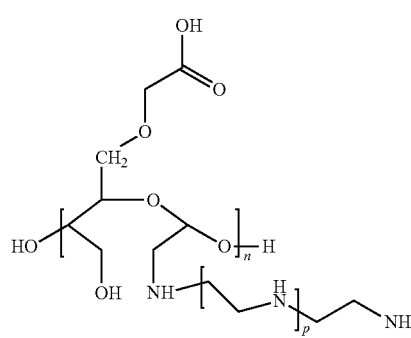 |

TABLE B-continued

Examples of repeating units (b)

| Substituent position | Substituent | Repeating unit of formula (b) |
|---|---|---|
| 2 | Polyethylene-imine | |
| 6 | N,N-Diethyl-aminoethyl | |

According to a preferred embodiment, the said repeating units (a) and (b) comprise at least one group containing nitrogen, which is ionizable at physiological pH, and which facilitates the complexation of the said anionic compound, and at least one group containing nitrogen, which is ionizable at a pH below physiological pH, and which facilitates the release of the complex from endosomes.

Preferably, the said groups containing nitrogen that are ionizable at physiological pH are present in numerical percentages of from 1% to 30% relative to the total number of hydroxyl groups in the glycogen used to prepare the cationic polymers according to the present invention.

Preferably, the said groups containing nitrogen that are ionizable at a pH below physiological pH are present in numerical percentages of from 0.1% to 10% relative to the total number of hydroxyl groups in the glycogen used to prepare the cationic polymers according to the present invention.

For the purposes of the present invention, the said groups containing nitrogen, which are ionizable at physiological pH, are $NH_2$—$(C_1$-$C_6)$alkyl, [N,N-di$(C_1$-$C_6)$alkylamino]-$(C_1$-$C_6)$alkyl, $NH_2$—[$(C_1$-$C_6)$alkylamino]-$(C_1$-$C_6)$alkyl, {[N,N-di$(C_1$-$C_6)$alkylamino]-$(C_1$-$C_6)$alkylamino}-$(C_1$-$C_6)$alkyl and azocyclyl-$(C_1$-$C_6)$alkyl.

Advantageously, the said groups containing nitrogen, which are ionizable at a pH below physiological pH, are $NH_2$—{[$(C_1$-$C_3)$alkyl]-di$(C_1$-$C_6)$alkylammonio}-$(C_1$-$C_6)$alkyl and {[N,N-di$(C_1$-$C_6)$alkylamino]-$(C_1$-$C_3)$alkyl-di$(C_1$-$C_6)$alkyl-ammonio}-$(C_1$-$C_6)$alkyl.

Advantageously, the novel cationic derivatives of glycogen according to the present invention have a low viscosity and may consequently be formulated in pharmaceutical compositions for injectable use. In particular, the novel cationic derivatives of glycogen according to the present invention have a viscosity of less than 10 mPa*s and preferably less than 5 mPa*s, measured at a concentration of 1% in PBS with a rotary rheometer.

The glycogen used to prepare the cationic polymers according to the present invention may be obtained according to one of the methods known in the art.

Preferably, the glycogen is prepared as described in international patent application WO 94/03502.

Preferably, the said glycogen is obtained from the species *Mytilus edulis* and *Mytilus galloprovincialis*.

Other sources of glycogen that may be used for the purposes of the present invention include shellfish, such as oysters and *Crepidula fornicata*, and the glycogen-rich organs of vertebrate animals, such as liver and muscles.

Preferably, the said glycogen is substantially free of compounds containing nitrogen and reducing sugars. As used in the present description and in the claims that follow, the expression "substantially free of compounds containing nitrogen and reducing sugars" indicates that the nitrogen content is less than 60 ppm, measured by means of the Kjeldahl method, and the content of reducing sugars is less than 0.25%, measured by means of the method of F. D. Snell and Snell ("*Colorimetric Methods of Analysis*", New York, 1954, vol. III, p. 204).

Preferably, the glycogen used according to the present invention is also characterized by a carbon content from about 44% to about 45%, a molecular weight of about $(2.5\pm0.1)\times10^6$ daltons and an optical rotation $(\alpha)_D^{20}$ of $197\pm2.0$ (c=1, in water).

More preferably, the glycogen used according to the present invention is Polglumyt™ glycogen, produced by Aziende Chimiche Riunite Angelini Francesco A.C.R.A.F. S.p.A.

A person skilled in the art will readily understand that the present invention is not directed towards novel classes of compounds with therapeutic efficacy per se. Rather, the present invention relates to the use of a glycogen-based cationic polymer as described previously for forming a complex with at least one anionic compound.

In a second aspect, the present invention relates to a complex between a glycogen-based cationic polymer and an anionic compound, in which the said glycogen-based cationic polymer comprises at least one repeating unit chosen from the group consisting of (a) and (b), described previously.

Preferably, the said anionic compound is organic or inorganic, with a low molecular weight or a high molecular weight.

More preferably, the said anionic compound is an active principle belonging, for example, to one of the following classes: anti-infectious agents, for example antibiotics and antivirals; analgesics; anorectics; anthelmintics; antiasthmatics; anticonvulsants; antidepressants; antidiabetics; antidiarrhoeals; antihistamines; anti-inflammatories; antihemicranic agents; anti-nauseous agents; antineoplastics; antiparkinsonians; anti-pruriginous agents; antipsychotics; antipyretics; antispasmolytics; anticholinergic agents; sympathomimetics; xanthine derivatives; drugs for the cardiovascular system, for example potassium, calcium-channel blockers, beta blockers, alpha blockers and antiarrhythmics; antihypertensives; diuretics and antidiuretics; central and peripheral vasodilators; central nervous system stimulants; vasoconstrictors; antitussive agents; decongestants; hormones; hypnotics; immunosuppressants; muscle relaxants; parasympatholytics; psychostimulants; sedatives; tranquillizers.

According to a preferred embodiment, the said anionic compound is a nucleic acid.

Preferably, the said nucleic acid is chosen from: oligonucleotides, RNA (siRNA, dsRNA, ssRNA, shRNA, miRNA, rRNA, hnRNA, mRNA, tRNA, snRNA, pre-mRNA, catalytic RNA, antisense RNA) and DNA (cDNA, mtDNA, ssDNA, dsDNA, antisense DNA, plasmid DNA).

The Applicant has observed that the said complex is capable of forming nanometric particles with a mean diameter (Z) of between 1 and 200 nm, preferably between 20 and 100 nm and more preferably between 30 and 50 nm.

According to a preferred embodiment, the said complex comprises an amount of the said anionic compound of between 5% and 60% by weight relative to the weight of the said glycogen-based cationic polymer.

Preferably, the said complex comprises an amount of the said anionic compound of between 10% and 50% by weight relative to the weight of the said glycogen-based cationic polymer.

More preferably, the said complex comprises an amount of the said anionic compound of between 10% and 30% by weight relative to the weight of the said glycogen-based cationic polymer.

The complex between a glycogen-based cationic polymer and an anionic compound may advantageously be prepared as a pharmaceutical composition.

In a third aspect, the present invention relates to a pharmaceutical composition comprising a complex between a glycogen-based cationic polymer and an anionic compound, and at least one pharmaceutically acceptable excipient, in which the said glycogen-based cationic polymer comprises at least one repeating unit chosen from the group consisting of (a) and (b), described previously.

In one preferred embodiment, the said anionic compound is a nucleic acid.

The term "excipient" means any agent known in the art that is suitable for preparing a pharmaceutical form.

Examples of excipients that are suitable according to the present invention are: preservatives, stabilizers, surfactants, osmotic pressure-regulating salts, emulsifiers, sweeteners, flavourings, dyes and the like.

The said pharmaceutical composition may be prepared in unit dosage form according to methods known in the art.

Preferably, the said pharmaceutical composition is for injectable use, such as for instance an aqueous solution, suspension or emulsion, or may be in the form of a powder to be reconstituted for the preparation of an aqueous solution, suspension or emulsion for intravenous, intramuscular, subcutaneous, transdermal or intraperitoneal administration.

Alternatively, the said pharmaceutical composition may be, for example, in the form of a tablet, a capsule, coated tablets, granules, solutions and syrups for oral administration; medicated plasters, solutions, pastes, creams or pomades for transdermal administration; suppositories for rectal administration; a sterile solution for aerosol administration; for immediate and sustained release.

In a fourth aspect, the present invention relates to the use of a complex between a glycogen-based cationic polymer and an anionic compound, for delivering or transferring the said anionic compound to a specific pharmacological target, for example an organ, a tissue or a cell, in which the said glycogen-based cationic polymer comprises at least one repeating unit chosen from the group consisting of (a) and (b), described previously.

According to a preferred embodiment, the said anionic compound is an active principle. Advantageously, the said anionic compound is a nucleic acid. Advantageously, the said pharmacological target is a cell.

In a preferred embodiment, the glycogen-based cationic polymer according to the present invention may be conjugated, directly or via a spacer, to a directing group that is capable of binding in a highly specific manner a target present on the cell surface and of facilitating the absorption of the complex into a specific cell (for example tumour cells, liver cells, haematopoietic cells, and the like).

The directing group may also be used for directing the cationic polymer to a cell compartment (for example the nucleus, mitochondria and the like).

The directing groups may be chosen, for example, from folic acid, monosaccharides, oligosaccharides, peptides, proteins and hyaluronic acid oligomers.

The examples that follow are intended to illustrate the present invention without, however, limiting it in any way.

EXAMPLES

Example 1

Preparation of Glycogen-Based Cationic Polymers Comprising the Unit (a)

(i) Synthesis of Glycogen-Based Cationic Polymers Comprising Groups Containing Nitrogen 10 g of Polglumyt™ glycogen (61.73 mmol of glucose) were dissolved in 124 mL of 1N NaOH (for the synthesis of products 1-7, 9-11 and 13-15) or 2N NaOH (for the synthesis of products 8, 12 and 16) in a two-necked round-bottomed flask equipped with a magnetic stirrer and a reflux condenser. Once the dissolution was complete, the mixture was heated to 70° C. and stirred for 2 hours.

Depending on the desired product, one of the following reagents (I) to (VI) was added, in the amounts (expressed as mmol of reagent) reported in Table 1:

(I) 2-chloro-N,N-diethylethylamine hydrochloride;
(II) 3-chloro-N,N-dimethylpropylamine hydrochloride;
(III) 2-chloro-N,N-dimethylethylamine hydrochloride;
(IV) solution of 3-chloro-2-hydroxypropyltrimethylammonium chloride at 60% by weight in $H_2O$;
(V) 1-(2-chloroethyl)piperidine; and
(VI) 4-(2-chloroethyl)morpholine.

The mixture was stirred at 70° C. overnight.

The next day, the heating was stopped and the mixture was allowed to cool to room temperature. The crude reaction product was then poured slowly into 400 mL of acetone. Once the addition was complete, the suspension obtained was stirred for about 30 minutes. After stopping the stirring, the mixture was left to sediment until separation of the supernatant and the precipitate was obtained.

The supernatant was discarded and the precipitate obtained was washed twice with acetone (200 mL). The solid thus obtained was filtered off, dissolved in 200 mL of distilled water, brought to neutral pH with 1N HCl solution and finally subjected to dialysis in regenerated cellulose tubes (cut-off 15,000) against distilled water until the conductivity was constant (equal to about 2-3 µS). The solution obtained was filtered through a 0.45 μm filter, concentrated under vacuum and finally freeze-dried.

The synthetic yields are collated in Table 1 below.

TABLE 1

| Class | Polymer No. | Reagent | mmol of reagent | Yield % (W/W) |
|---|---|---|---|---|
| Diethylaminoethyl | 1 | (I) | 2.65 | 82 |
| (DEAE) | 2 | (I) | 15.43 | 80 |
| glycogen | 3 | (I) | 30.87 | 80 |
|  | 4 | (I) | 61.73 | 82 |
| Dimethyl- | 5 | (II) | 15.43 | 82 |
| aminopropyl | 6 | (II) | 30.87 | 83 |
| (DMAP) | 7 | (II) | 61.73 | 80 |
| glycogen | 8 | (II) | 123.46 | 82 |
| Dimethyl- | 9 | (III) | 15.43 | 81 |
| aminoethyl | 10 | (III) | 30.87 | 80 |
| (DMAE) | 11 | (III) | 61.73 | 83 |
| glycogen | 12 | (III) | 123.46 | 80 |
| 2-Hydroxypropyl- | 13 | (IV) | 15.43 | 83 |
| trimethylammonium | 14 | (IV) | 30.87 | 84 |
| (2-OH-PTMA) | 15 | (IV) | 61.73 | 82 |
| glycogen | 16 | (IV) | 123.46 | 84 |
| Glycogen | 40 | (V) | 30.87 | 83 |

TABLE 1-continued

| Class | Polymer No. | Reagent | mmol of reagent | Yield % (W/W) |
|---|---|---|---|---|
| heterocyclic derivative | 41 | (VI) | 30.87 | 80 |

Via the method described, the cationic polymers 1-16 and 40-41 having the structures illustrated in Table 2 below were prepared.

In the represented structures, the abbreviation "Glu" indicates that the polymer chain may continue with repeating units of unmodified glucose or with repeating units according to the present invention. In addition, to facilitate the visualization, the branches are not represented and the substituents are represented only in position 6 and on different repeating units.

A person skilled in the art will readily understand that the same repeating unit can comprise from one to three substituents, which may be identical or different, and that these substituents may be independently present on positions 2, 3 and/or 6.

TABLE 2
| Class | Structural formula | Polymer No. | ¹H-NMR |
|---|---|---|---|
| (DEAE) Glycogen | | 1 | δ ppm: 1.45-1.75 (CH₃, multiplet), 3.2-4.6 (multiplet), 5.2-6.1 (multiplet) |
| | | 2 | |
| | | 3 | δ ppm: 1.25-1.75 (CH₃, multiplet), 2.8-4.6 (multiplet), 5.2-6.1 (multiplet) |
| | | 4 | |
| (DMAP) Glycogen | | 5 | δ ppm: 2.2-4.5 (multiplet), 5.2-6.1 (multiplet H anomeric) |
| | | 7 | |
| | | 6 | δ ppm: 2.2-4.4 (multiplet), 5.2-6.1 (multiplet H anomeric) |
| | | 8 | |
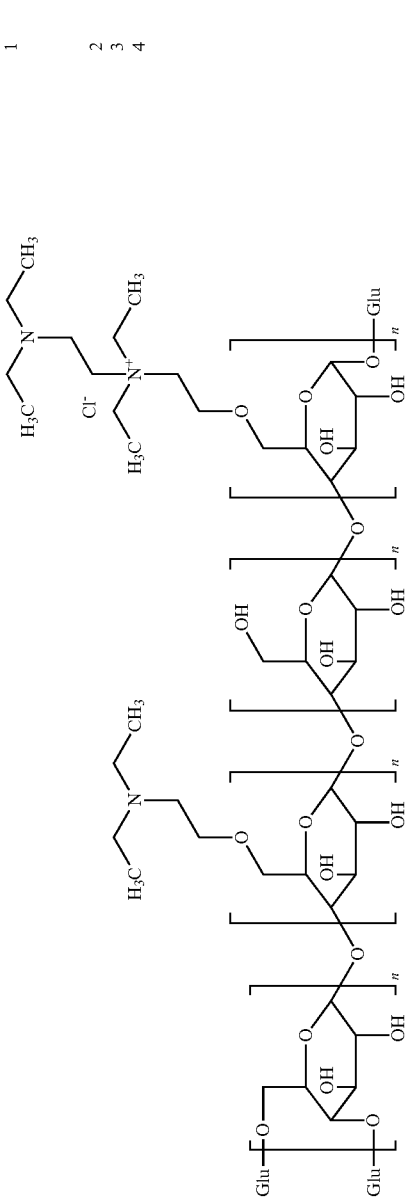
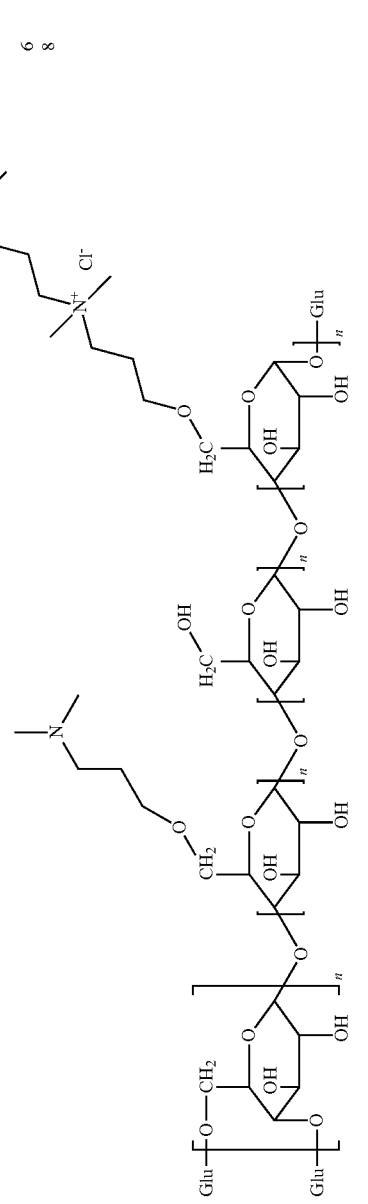

TABLE 2-continued
| Class | Structural formula | Polymer No. | $^1$H-NMR |
|---|---|---|---|
| (DMAE) Glycogen | | 9 10 11 12 | δ ppm: 2.5-4.6 (multiplet), 5.2-6.2 (multiplet H anomeric) |
| (2-OH-PTMA) Glycogen | | 13 14 15 16 | δ ppm: 3.45-4.5 (multiplet), 5.25-6.1 (multiplet H anomeric) |
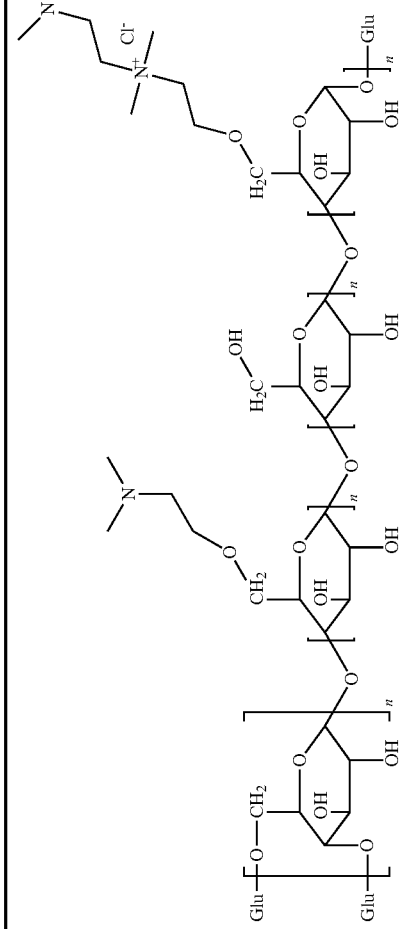
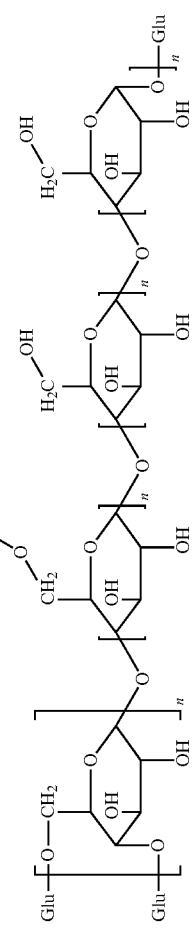

TABLE 2-continued

| Class | Structural formula | Polymer No. | $^1$H-NMR |
|---|---|---|---|
| Glycogen heterocyclic derivative | | 40 | δ ppm 1.65-2.35 (multiplet), 2.6-3.15 (multiplet), 3.55-4.45 (multiplet), 5.2-6.15 (multiplet H anomeric) |
| | | 41 | δ ppm 2.8-3.1 (multiplet), 3.6-4.45 (multiplet), 5.2-6.1 (multiplet H anomeric) |

(ii) Synthesis of Glycogen-Based Cationic Polymers Comprising Groups Containing Nitrogen and Carboxymethyl Groups Polglumyt™ glycogen containing at least one carboxymethyl group (Glycogen-CM) was synthesized as described below.

9.57 g (59.07 mmol of glucose) of anhydrous Polglumyt™ glycogen, dried beforehand in an oven at 60° C. under vacuum to constant weight, were placed in a two-necked round-bottomed flask equipped with a magnetic stirrer and under a stream of nitrogen, and dissolved in 200 mL of anhydrous dimethyl sulfoxide. Once the dissolution was complete, sodium hydride was added in the amounts reported in Table 3, and the mixture was stirred for 1 hour at room temperature. Next, sodium chloroacetate was added in the amounts reported in Table 3, and the mixture was stirred overnight at room temperature.

The next day, the mixture was poured slowly into acetone (800 mL) and the suspension obtained was stirred for about 30 minutes. The solid obtained was filtered off, washed twice with acetone (400 mL), filtered off again and dissolved in distilled water (200 mL). The solution obtained was subjected to dialysis in regenerated cellulose tubes (cut-off 15,000) against distilled water, until the conductivity was constant (equal to about 2-3 µS). The solution obtained was filtered through a 0.45 µm filter, concentrated under vacuum and finally freeze-dried.

The degree of derivatization (DD), understood as being the number of glucose molecules derivatized with a carboxymethyl group per 100 glucose monomers, was determined by IR spectroscopy, by generating a calibration curve with mixtures containing a known titre of Polglumyt™ glycogen and sodium acetate.

TABLE 3

| Glycogen-CM | mmol NaH | mmol ClCH$_2$COONa | Yield % (W/W) | DD |
|---|---|---|---|---|
| 100 | 5.91 | 6.50 | 83 | 1 |
| 101 | 11.82 | 13.00 | 80 | 14 |
| 102 | 17.72 | 19.49 | 78 | 22 |
| 103 | 23.63 | 25.99 | 75 | 32 |
| 104 | 29.54 | 32.49 | 74 | 39 |

The glycogen-CM thus obtained was used in the following syntheses, to obtain cationic polymers comprising nitrogen groups.

Glycogen-CMs comprising diethylaminoethyl (DEAE-glycogen-CM) and 2-hydroxypropyltrimethylammonium (2-OH-PTMA-glycogen-CM) groups were synthesized in particular.

DEAE-Glycogen-CM 1 g of product 103 was dissolved in 10.8 mL of 1N NaOH in a two-necked round-bottomed flask equipped with a magnetic stirrer and a reflux condenser, and heated at 70° C. for 2 hours.

0.929 g of 2-chloro-N,N-diethylethylamine hydrochloride (5.4 mmol) were added and the mixture was stirred overnight at 70° C.

The next day, the heating was stopped and the mixture was allowed to cool to room temperature. The crude reaction product was then poured slowly into 100 mL of acetone. At the end of the addition, the suspension obtained was stirred for 30 minutes.

The solid obtained was filtered off, washed twice with acetone (100 mL), dissolved in 50 mL of distilled water, brought to a pH of 6.5-7 with 1N hydrochloric acid, and finally subjected to dialysis in regenerated cellulose tubes (cut-off 15,000) against distilled water until the conductivity was constant (equal to about 2-3 µS). The solution obtained was filtered through a 0.45 µm filter, concentrated under vacuum and finally freeze-dried.

2-OH-PTMA-Glycogen-CM 2.5 g of product 103 were dissolved in 27 mL of 1N NaOH in a two-necked round-bottomed flask equipped with a magnetic stirrer and a reflux condenser, and heated at 70° C. for 2 hours.

Next, a solution of 3-chloro-2-hydroxypropyltrimethylammonium chloride (60% by weight in H$_2$O, =8.1 mmol) was added and the mixture was stirred at 70° C. overnight.

The next day, the heating was stopped and the mixture was allowed to cool to room temperature. The crude reaction product was then poured slowly into 80 mL of acetone.

The solid obtained was filtered off, washed twice with acetone (80 mL), dissolved in 50 mL of distilled water and subjected to dialysis in regenerated cellulose tubes (cut-off 15,000) against distilled water until the conductivity was constant (equal to about 2-3 µS). The solution obtained was filtered through a 0.45 µm filter, concentrated under vacuum and finally freeze-dried.

The cationic polymers 17 and 19 obtained via the described methods are shown in Table 4 below.

To facilitate the visualization, the branches are not shown, and the substituents are shown only in position 6 and on different repeating units. In the structures shown, the abbreviation "Glu" indicates that the polymer chain may continue with repeating units of unmodified glucose or with repeating units according to the present invention.

A person skilled in the art will readily understand that the same repeating unit may comprise from one to three substituents, which may be identical or different, and that these substituents may be independently present on positions 2, 3 and/or 6 of the same repeating unit.

TABLE 4

| Class | Structural formula | Polymer No. | ¹H-NMR |
|---|---|---|---|
| DEAE-Glycogen-CM | [structural formula of DEAE-Glycogen-CM showing glucose repeating units with diethylaminoethyl and carboxymethyl substituents, including a quaternized ammonium group with Cl⁻ counterion and carboxylate with Na⁺] | 17 | δ ppm: 1.25-1.75 (multiplet), 3-4.65 (multiplet), 5.5-6.15 (multiplet H anomeric) |
| 2-OH-PTMA-Glycogen-CM | [structural formula of 2-OH-PTMA-Glycogen-CM showing glucose repeating units with 2-hydroxypropyltrimethylammonium (Cl⁻) and carboxymethyl (Na⁺) substituents] | 19 | δ ppm: 3.4-4.65 (multiplet), 5.25-6.20 (multiplet H anomeric) |

Example 2

Preparation of Glycogen-Based Cationic Polymers Comprising the Unit (b)

Polglumyt™ glycogen was oxidized with potassium periodate according to the following method.

20 g of Polglumyt™ glycogen (123.46 mmol of glucose) were dissolved in 400 mL of distilled water in a dark glass bottle. Potassium periodate was added in the amounts given in Table 5 (expressed in mmol of reagent) and the mixture was stirred for 30 minutes at room temperature.

The reaction was stopped by adding an excess of ethylene glycol (26 mL) with continued stirring for 2 hours at room temperature.

The mixture was subjected to dialysis in regenerated cellulose tubes (cut-off 15,000) against distilled water, until the conductivity was constant (equal to about 2-3 μS). The mixture was then filtered through a 0.45 μm filter and freeze-dried.

Next, the degree of oxidation (% of oxidized glucose monomers) was determined by titration with 0.1N NaOH of the hydrochloric acid released by the reaction between hydroxylamine hydrochloride and the free aldehyde groups present on the various carbohydrates. The reaction is given below:

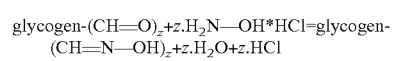

glycogen-(CH=O)$_z$+z.H$_2$N—OH*HCl=glycogen-(CH=N—OH)$_z$+z.H$_2$O+z.HCl

The percentage of oxidized monomers was determined via the following formula:

$$DD = \frac{V \times N \times 0.5}{W/162} \times 100$$

in which
V=mL of NaOH;
N=normality of NaOH;
W=mg of anhydrous sample;
162=molecular weight of the glucose repeating unit

TABLE 5

| oxidized glycogen | mmol KIO$_4$ | % yield (W/W) | DD |
|---|---|---|---|
| 200 | 6.17 | 88 | 5 |
| 201 | 12.35 | 87 | 10 |
| 202 | 24.69 | 88 | 18 |

The oxidized Polglumyt™ glycogen thus obtained was reacted with one of the reagents (VII) to (X) below, in the amounts (expressed in mmol of reagent) given in Table 6:
(VII) spermine (Fluka, reference No. 85590);
(VIII) tetraethylenepentamine (Fluka, reference No. 15652843);
(IX) solution of polyethyleneimine MW 1300 at 50% by weight in water (Aldrich, reference No. 482595);
(X) solution of polyethyleneimine MW 2000 at 50% by weight in water (Aldrich, 408700).

The derivatives were synthesized according to the following general method.

2 g of oxidized Polglumyt™ glycogen were dissolved in 200 mL of borate buffer at pH 8.5 in a three-necked round-bottomed flask equipped with a mechanical stirrer (IKA Labortechnik model). The amine was dissolved in 40 mL of borate buffer, added slowly to the reaction flask, and the mixture was stirred mechanically at room temperature.

After 4 hours, sodium borohydride (473 mg; 12.5 mmol) was added and the mixture was stirred mechanically overnight at room temperature.

The next day, the crude reaction product was poured slowly into 400 mL of acetone and the suspension obtained was stirred for 30 minutes. The solid obtained was filtered off, washed twice with acetone (400 mL), filtered off again and dissolved in distilled water (100 mL). The solution was neutralized with 1N HCl and subjected to dialysis in regenerated cellulose tubes (cut-off 15,000) against distilled water until the conductivity was constant (equal to about 2-3 µS). The solution obtained was filtered through a 0.45 µm filter and finally freeze-dried.

TABLE 6

| No. | Starting oxidized glycogen | Reagent | mmol reagent | % yield (W/W) |
|---|---|---|---|---|
| 20 | 200 | VII | 0.60 | 69 |
| 21 | 200 | IX | 0.48 | 84 |

TABLE 6-continued

| No. | Starting oxidized glycogen | Reagent | mmol reagent | % yield (W/W) |
|---|---|---|---|---|
| 22 | 200 | X | 0.31 | 70 |
| 23 | 201 | VII | 0.60 | 65 |
| 24 | 201 | VIII | 0.41 | 70 |
| 25 | 201 | VIII | 0.83 | 44 |
| 26 | 201 | IX | 0.48 | 83 |
| 27 | 201 | X | 0.31 | 87 |
| 28 | 202 | VII | 1.20 | 24 |
| 29 | 202 | IX | 0.48 | 95 |
| 30 | 202 | IX | 0.96 | 98 |

The cationic polymers 20-30 obtained via the described methods are shown in Table 7 below. In the structures shown, the abbreviation "Glu" indicates that the polymer chain may continue with repeating units of unmodified glucose or with repeating units according to the present invention. To facilitate the visualization, the branches are not shown, and the substituents are shown on different repeating units.

TABLE 7

| Class | Structural formula | Polymer No. | IR |
|---|---|---|---|
| Oxidized glycogen | [structure with Glu, H₂C-OH, OH, NH, H₂N groups] | 24 | 3293 (M), 2926 (W), 1638 (W), 1409 (W), 1359 (W), 1240 (W), 1148 (M), 1078 (M), 1016 (VS), 999 (VS), 930 (M), 848 (M), 759 (M) |
| | | 25 | 3308 (M), 2924 (W), 1639 (W), 1411 (W), 1358 (W), 1243 (W), 1149 (M), 1078 (S), 1016 (VS), 999 (VS), 930 (M), 848 (M), 759 (M) |
| Oxidized glycogen | [structure with Glu, H₂C-OH, OH, NH, H₂N groups] | 20 | 3306 (M), 2925 (W), 1639 (W), 1411 (W), 1361 (W), 1241 (W), 1148 (M), 1078 (S), 995 (VS), 927 (M), 847 (M), 757 (M) |
| | | 23 | 3293 (M), 2926 (W), 1638 (W), 1412 (W), 1359 (W), 1241 (W), 1148 (M), 1078 (S), 1015 (VS), 929 (M), 848 (M), 759 (M) |
| | | 28 | 3292 (M), 2928 (W), 1639 (W), 1415 (W), 1355 (W), 1243 (W), 1148 (M), 1078 (S), 1015 (VS), 929 (M), 848 (M), 758 (M) |

TABLE 7-continued
| Class | Structural formula | Polymer No. | IR |
|---|---|---|---|
| Oxidized glycogen | 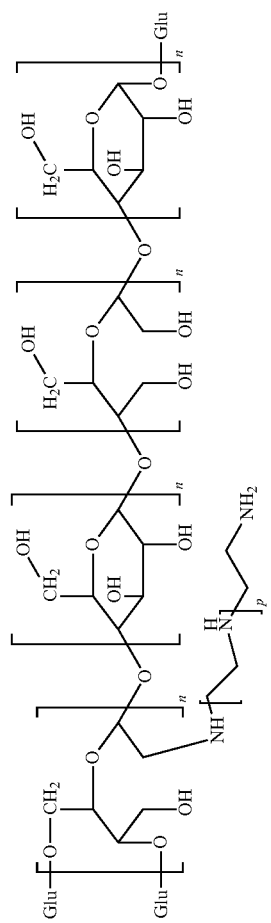 | 21 | 3228 (M), 2924 (W), 1640 (M), 1412 (W), 1361 (W), 1148 (M), 1079 (S), 1015 (VS), 999 (VS), 930 (M), 848 (M), 759 (M) |
| | | 26 | 3298 (M), 2925 (W), 1638 (W), 1411 (W), 1359 (W), 1148 (M), 1079 (S), 1016 (VS), 999 (VS), 930 (M), 848 (M), 759 (M) |
| | | 22 | 3292 (M), 2921 (W), 1643 (W), 1411 (W), 1360 (W), 1148 (M), 1078 (S), 1015 (VS), 998 (VS), 930 (M), 848 (M), 759 (M) |
| | | 27 | 3299 (M), 2924 (W), 1635 (W), 1412 (W), 1358 (W), 1148 (M), 1079 (S), 1016 (VS), 1000 (VS), 930 (M), 847 (M), 759 (M) |
| | | 29 | 3289 (W), 2924 (W), 2840 (W), 1635 (W), 1411 (W), 1336 (W), 1147 (M), 1079 (S), 1016 (VS), 1000 (VS), 930 (M), 848 (M), 758 (M) |
| | | 30 | 3276 (M), 2924 (W), 2843 (W), 1634 (W), 1453 (W), 1333 (M), 1146 (M), 1079 (S), 1019 (VS), 1000 (VS), 930 (M), 848 (M), 758 (M) |

Example 3

Determination of the Degree of Derivatization (DD) of Cationic Polymers Containing Repeating Units of Type (a)

The degree of derivatization, relative to the number of groups containing nitrogen present in the polymers containing repeating units (a), was calculated by transformation of the amine groups into the corresponding hydrochloride and by determining the amount of halogen ions present either on the amine groups or on the quaternary ammonium groups.

The same procedure was applied to DEAE-dextran hydrochloride (commercial product DEAE-Dextran Hydrochloride, Sigma, reference No. D9885), used as comparative product.

The amount of halogen ions was determined on the dry weight of the polymer, obtained by subtracting the water content determined via the Karl Fischer method.

1 g of amine derivative was dissolved in 10 mL of distilled water. Once the dissolution was complete, 10 mL of 1N hydrochloric acid were added and the mixture was stirred for 30 minutes. Once the stirring was complete, the mixture was poured into acetone (100 mL). The solid obtained was filtered off, washed twice with acetone (100 mL) and dried in an oven at 60° C. under vacuum.

The amount of halogen ions is expressed as a weight percentage, that is to say as the weight of halogen ions per 100 g of cationic polymer.

For the purposes of the determination, each nitrogen atom was considered as being independently substituted.

The degree of derivatization was calculated according to the equation given below.

$$DD = \left[ \frac{\frac{H.I.(\text{hydrated weight}) * 100 *}{MW(\text{hydrochloride monomer})}}{100 - \% \ H_2O} \Bigg/ 35.45 \right] \Bigg/ 3$$

DD=degree of derivatization
H.I.=grams of halogen ions per 100 g of hydrated sample
MW=molecular weight of the monomer substituted with a single alkylamine hydrochloride group
35.45=molecular weight of chlorine
The results obtained are given in Table 8 below.

TABLE 8

| Polymer No. | DD |
|---|---|
| 1 | 1 |
| 2 | 6 |
| 3 | 12 |
| 4 | 22 |
| 5 | 5 |
| 6 | 6 |
| 7 | 12 |
| 8 | 19 |
| 9 | 4 |
| 10 | 7 |
| 11 | 12 |
| 12 | 14 |
| 13 | 3 |
| 14 | 5 |
| 15 | 13 |
| 16 | 15 |
| 18(*) | 20 |

(*)comparative: DEAE-dextran

The influence of the degree of derivatization and of the functional group was studied as a function of two operating parameters, (i) the tendency toward aggregation, which must be minimized; and (ii) the charge capacity, which must be maximized.

Example 4

Dynamic Light Scattering (DLS) Measurement

Dynamic light scattering studies were used to study the aggregation tendency of the cationic polymers.

The dynamic light scattering studies were performed as reported below on cationic polymers based on Polglumyt™ glycogen, prepared as described in Example 1, and on respective complexes with an siRNA (Invitrogen, supplier reference No. 1299001), prepared at various siRNA/polymer weight percentage ratios.

For the light scattering studies, the following solutions were prepared:
solution 1: stock solution of siRNA 0.1 mg/mL, in RNase-free PBS;
solution 2: stock solution of various cationic polymers at a concentration of 0.2 mg/mL, in RNase-free PBS, filtered through sterile 0.22 µm filters;
solution 3: solution of RNase-free PBS, filtered through sterile 0.22 µm filters.

The abbreviation PBS (Phosphate-Buffered Saline) represents a standard phosphate-buffered saline at pH 7.4 comprising an aqueous saline solution of sodium chloride 8 g/l, sodium phosphate 1.78 g/l, potassium chloride 0.2 g/l and potassium phosphate 0.27 g/l.

The samples that were analysed were obtained by mixing solutions 1, 2 and 3 according to the ratios given in Table 9. The samples were then treated for 30 seconds by stirring and left to stand for 30 minutes, twice. After a subsequent treatment by stirring for 30 seconds and leaving to stand for 1 hour, the samples were analysed with a DLS Zetasizer Nano Malvern, care being taken to treat the solutions by stirring 5 minutes before the analysis.

The measurements were taken using a helium-neon laser ($\lambda$=632.8 nm) at 25° C. and at a scattering angle of 173°. The results were processed using the Zetasizer software.

TABLE 9

| | | Composition | | |
|---|---|---|---|---|
| siRNA mg/mL | Polymer mg/mL | mL of solution 1 | mL of solution 2 | mL of solution 3 |
| — | 0.1 | — | 0.5 | 0.5 |
| 0.050 | 0.1 | 0.5 | 0.5 | — |
| 0.03 | 0.1 | 0.3 | 0.5 | 0.2 |
| 0.02 | 0.1 | 0.2 | 0.5 | 0.3 |
| 0.015 | 0.1 | 0.15 | 0.5 | 0.35 |
| 0.010 | 0.1 | 0.10 | 0.5 | 0.4 |
| 0.005 | 0.1 | 0.05 | 0.5 | 0.45 |

The study makes it possible to determine the following parameters:
1. the mean diameter (Z) of the cationic derivatives of Polglumyt™ glycogen free of siRNA (the results are collated in Table 10);
2. the aspect ratio of the nanoparticles (the results are collated in Table 10); and
3. the maximum weight percentage ratio of siRNA relative to the weight of polymer for which no aggregation phenomenon is observed (the results are collated in Table 10).

TABLE 10

| Polymer No. | (1) Mean diameter (Z) (nm) | (2) Aspect ratio | (3) Ratio % siRNA/polymer (w/w) without formation of aggregates |
|---|---|---|---|
| 1 | 37 | 1.2 | 10 |
| 2 | 37 | 0.8 | 50 |
| 3 | 38 | 0.9 | 15 |
| 4 | 41 | 0.8 | 20 |
| 5 | 35 | 0.9 | 50 |
| 6 | 36 | 0.8 | 10 |
| 7 | 38 | 0.9 | 10 |
| 8 | 38 | 0.9 | 15 |
| 9 | 35 | 1.1 | 50 |
| 10 | 36 | 0.8 | 50 |
| 11 | 37 | 0.8 | 50 |
| 12 | 40 | 0.9 | 15 |
| 13 | 36 | 0.8 | 50 |
| 14 | 37 | 0.9 | 50 |
| 15 | 41 | 0.8 | 10 |
| 16 | 41 | 0.9 | 15 |
| 17 | 35 | 1.0 | 50 |
| 18(*) | 76 | 4.5 | 20 |

(*)comparative: DEAE-dextran (1) Mean Diameter (Z)

As may be seen from Table 10, all the derivatives have a mean diameter (Z) of less than 100 nm.

Advantageously, and in contrast with DEAE-dextran, the cationic derivatives according to the invention form nanoparticles with a mean diameter (Z) of less than 70 nm.

(2) Aspect Ratio

The aspect ratio is the width at mid-height of the distribution peak of the particle sizes normalized by the mean diameter and thus describes the shape of the size distribution peak.

As may be seen, all the cationic polymers according to the invention had size distributions with an aspect ratio of between 0.8 and 1.1, in contrast with DEAE-dextran, which showed a size distribution with an aspect ratio equal to 4.5.

This indicated that, by using the same synthetic method, the glycogen-based cationic polymers according to the present invention make it possible to obtain nanoparticles of controlled sizes within a size range close to the mean value.

(3) Maximum Weight Percentage Ratio of siRNA/Polymer for which No Aggregation is Observed The results showed that the cationic polymers comprising all the substituents according to the present invention formed aggregate-free complexes up to 50% by weight of siRNA, as a function of the degree of derivatization.

Polymer 18 (DEAE-dextran) formed aggregate-free complexes only up to 20% by weight of siRNA.

Example 5

Determination of the Charge Capacity

The charge capacity was determined for a series of derivatives containing the repeating units (a) and (b) via gel electrophoresis.

The complexes were prepared according to the following method.

The complexes between siRNA and the various polymeric derivatives were prepared using various siRNA/polymer ratios (weight %).

Polymer solutions at various concentrations, described in Tables 11 and 12, were mixed in RNase-free PBS, filtered through a 0.2 μm filter, with a solution of siRNA (Invitrogen, reference No. 1299001) at 0.340 mg/mL in RNase-free water. Next, the mixtures were treated by stirring for about 30 seconds, left to stand for 15 minutes at room temperature, treated again by stirring for 30 seconds, and, after leaving to stand for about 30 minutes, were subjected to gel electrophoresis.

The gels were developed by charging 10 μl of solution of each complex on to a 4% agarose gel containing a 1:200 000 ratio of Green Gel Plus™ Nucleic Acid Stain 20000× prepared in MOPS-EDTA-sodium acetate buffer.

The agarose gels were developed for one hour at a constant voltage of 80V. The images were obtained by means of the ImageQuant LAS 4000 system (GE Healthcare).

The gels obtained are shown in FIGS. 1 to 8.

The complexes between polymer 3 (DEAE-glycogen) and siRNA were prepared using the polymer solutions and siRNA, with the amounts given in Table 11 below. Polymer 3 was charged with 0.5% to 800% by weight of siRNA.

The gels on which the complexes between polymer 3 and siRNA were seeded and which were subsequently developed by electrophoresis are shown in the figures listed in Table 11.

TABLE 11

| mg/mL polymer | mg/mL siRNA | % siRNA (w/w) | FIG. |
|---|---|---|---|
| 20 | 0.1 | 0.5 | 1 |
| 10 | 0.1 | 1 | 1 |
| 5 | 0.1 | 2 | 1 |
| 2.5 | 0.1 | 4 | 1 |
| 1.25 | 0.1 | 8 | 1 |
| 1 | 0.1 | 10 | 2 |
| 0.66 | 0.1 | 15 | 2 |
| 0.5 | 0.1 | 20 | 2 |
| 0.333 | 0.1 | 30 | 3 |
| 0.2 | 0.1 | 50 | 3 |
| 0.1 | 0.1 | 100 | 3 |
| 0.05 | 0.1 | 200 | 3 |
| 0.025 | 0.1 | 400 | 3 |
| 0.0125 | 0.1 | 800 | 3 |

Unmodified Polglumyt™ glycogen (50*) was used as comparative:

| Polymer | mg/mL polymer | mg/mL siRNA | % siRNA (w/w) | FIG. |
|---|---|---|---|---|
| 50 (*) | 1 | 0.1 | 10 | 2 |
|  | 0.0125 | 0.1 | 800 | 2 |

In FIG. 1, it may be seen that, in the columns of polymer 3 complexed with siRNA at a percentage from 0.5% to 8% by weight, the white band corresponding to siRNA alone was not present. The absence of the band indicated that polymer 3 was capable of fully complexing siRNA from 0.5% to 8% by weight relative to the weight of polymer.

Figure 2:
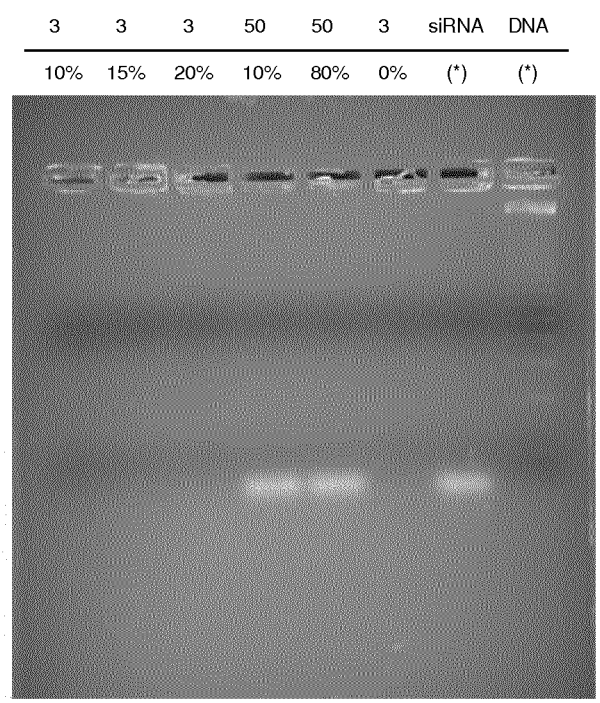

In FIG. 2, the absence of the band corresponding to siRNA in the columns of polymer 3 complexed with siRNA indicated that polymer 3 was capable of fully complexing siRNA in a percentage of from 10% to 20% by weight relative to the weight of the polymer. The presence of the band corresponding to siRNA in the columns of polymer 50 (unmodified Polglumyt™ glycogen) indicated that the unmodified Polglumyt™ glycogen was incapable of complexing siRNA even at a percentage equal to 10% by weight relative to the weight of the polymer.

Figure 3:
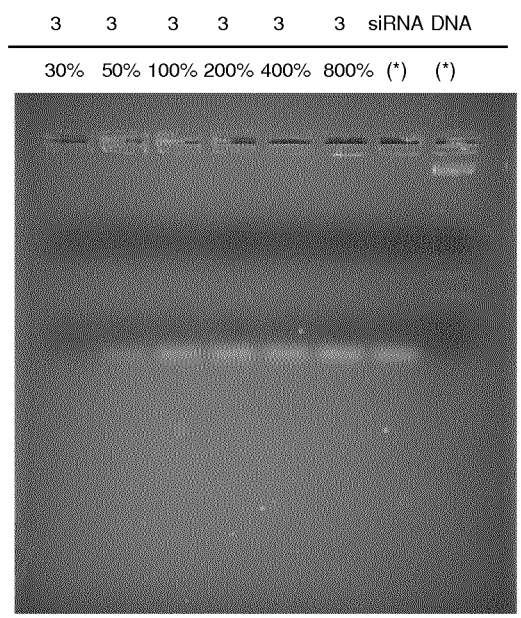

In FIG. 3, the absence of the band corresponding to siRNA in the columns of polymer 3 complexed with 30% of siRNA indicated that polymer 3 was capable of fully complexing 30% by weight of siRNA relative to the total weight of the polymer. In contrast, the presence of a band corresponding to siRNA at percentages of 50% to 800% indicated that polymer 3 was incapable of complexing 50% by weight of siRNA, relative to the total weight of the polymer.

These studies thus demonstrated that the maximum charge capacity of polymer 3 was 30% by weight of siRNA. In contrast, the unmodified Polglumyt™ glycogen (polymer 50) was incapable of complexing siRNA.

In addition, polymer-siRNA complexes were prepared using the following polymers:
- No. 1, 2, 6, 8, 10, 12, 14, 16, comprising the repeating unit (a);
- No. 20, 21, 23, 24, 25, 28, comprising the repeating unit (b);

Two siRNA charge percentages were used: 5% and 20% relative to the weight of the polymer. The solutions used are collated in Table 12 below.

TABLE 12

| Polymer | mg/mL polymer | mg/mL siRNA | FIG. |
|---|---|---|---|
| 1 | 2 | 0.1 | 4 |
|   | 0.5 | 0.1 | 4 |
| 2 | 2 | 0.1 | 4 |
|   | 0.5 | 0.1 | 4 |
| 6 | 2 | 0.1 | 4 |
|   | 0.5 | 0.1 | 4 |
| 8 | 2 | 0.1 | 6 |
|   | 0.5 | 0.1 | 6 |
| 10 | 2 | 0.1 | 5 |
|   | 0.5 | 0.1 | 5 |
| 12 | 2 | 0.1 | 6 |
|   | 0.5 | 0.1 | 6 |
| 14 | 2 | 0.1 | 5 |
|   | 0.5 | 0.1 | 5 |
| 16 | 2 | 0.1 | 6 |
|   | 0.5 | 0.1 | 6 |
| 20 | 2 | 0.1 | 8 |
|   | 0.5 | 0.1 | 8 |
| 21 | 2 | 0.1 | 7 |
|   | 0.5 | 0.1 | 7 |
| 23 | 2 | 0.1 | 8 |
|   | 0.5 | 0.1 | 8 |
| 24 | 2 | 0.1 | 7 |
|   | 0.5 | 0.1 | 7 |
| 25 | 2 | 0.1 | 7 |
|   | 0.5 | 0.1 | 7 |
| 28 | 2 | 0.1 | 8 |
|   | 0.5 | 0.1 | 8 |

Figure 4:
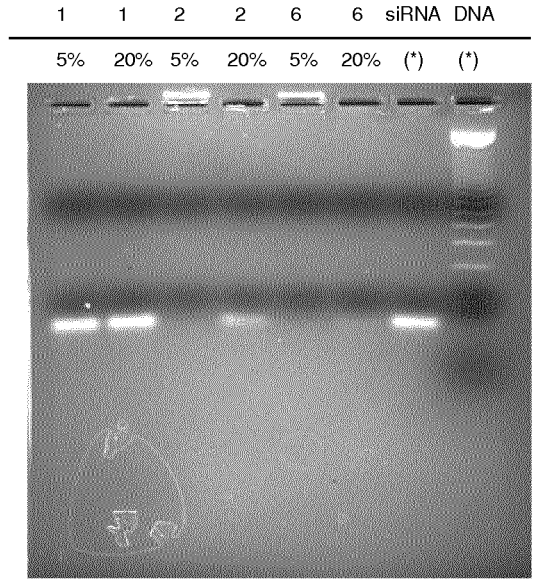

In FIG. 4, the presence of the band corresponding to siRNA in the columns of polymer 1 complexed, respectively, with 5% and 20% by weight of siRNA indicated that polymer 1 (DEAE-Polglumyt with a low degree of derivatization) was incapable of complexing siRNA. Polymer 2 was capable of complexing siRNA at a percentage of 5% by weight relative to the total weight of the polymer, and polymer 6 was capable also of complexing 20% by weight of siRNA relative to the total weight of the polymer.

Figure 5:
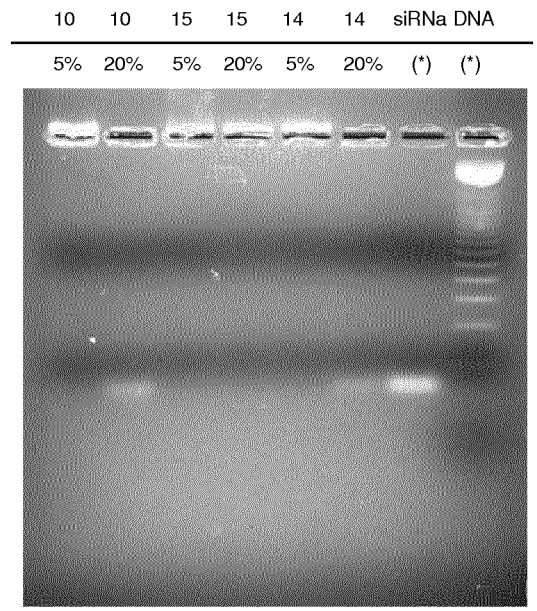

In FIG. 5, the presence of the band corresponding to siRNA in the columns of polymers 10 and 14 complexed with 20% by weight of siRNA indicated that these polymers were capable of complexing 5% by weight of siRNA. In contrast, polymer 15 was capable of complexing 20% by weight of siRNA.

Figure 6:
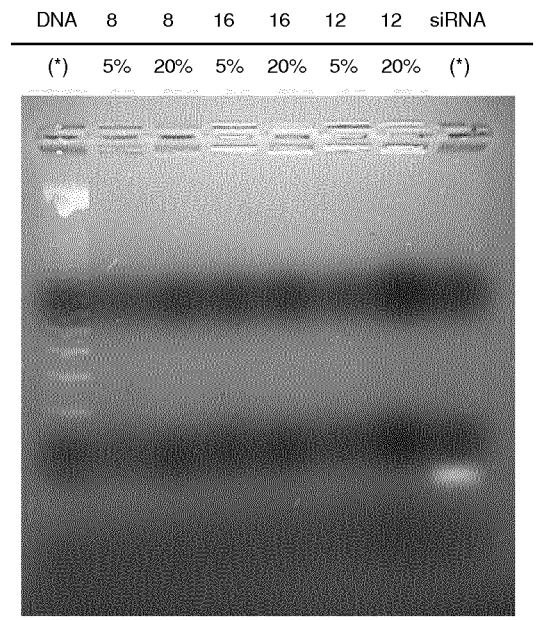

In FIG. 6, the absence of the band corresponding to siRNA indicated that polymers 8, 12 and 16 were capable of complexing 20% by weight of siRNA.

Figure 7:
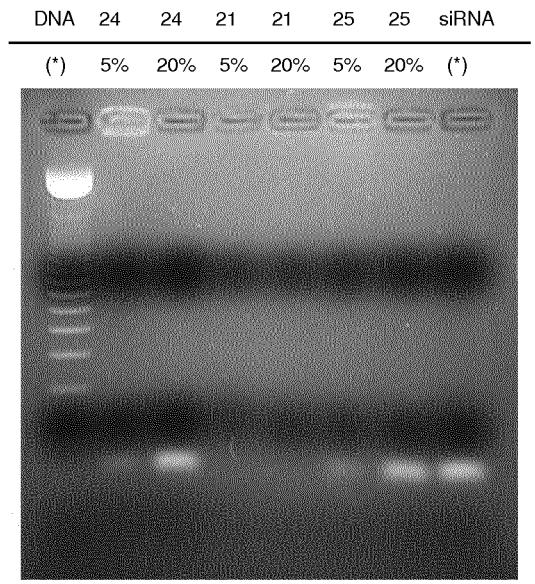

In FIG. 7, the presence of the band corresponding to siRNA in the columns of polymers 24 and 25 indicated that these polymers were incapable of complexing 5% of siRNA. In contrast, polymer 21 also complexed 20% of siRNA.

Figure 8:
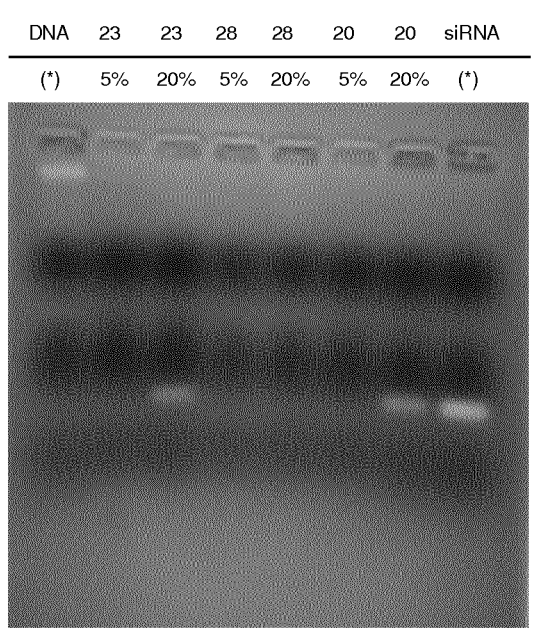

In FIG. 8, the presence of the band corresponding to siRNA in the columns of polymers 23 and 20 complexed with 20% of siRNA indicated that these polymers complexed 5% of siRNA. In contrast, polymer 28 complexed 20% of siRNA.

In general, thus, the studies made it possible to demonstrate that only polymers 1 (DEAE-glycogen with the lowest degree of derivatization), 24 and 25 were capable of complexing less than 5% by weight of siRNA.

All the other derivatives were capable of complexing 20% of siRNA, like the comparative polymer 18 (DEAE-dextran). In contrast, polymer 50 (unmodified Polglumyt™ glycogen) was incapable of forming complexes with siRNA.

Example 6

Cytotoxicity Studies with Cationic Derivatives of Polglumyt™ Glycogen

The cytotoxicity studies were performed on (DEAE)-glycogen (polymers 1-4), (DMAP)-glycogen (polymers 5-8), (DMAE)-glycogen (polymers 9-12), (2-OH-PTMA)-glycogen (polymers 13-16), on unmodified Polglumyt™ glycogen (polymer 50), on DEAE-dextran hydrochloride (polymer 18) and on another reference polymer that has been widely studied for the delivery of nucleic acids, branched polyethyleneimine (PEI) (Aldrich, reference No. 40872-7) (polymer 60).

(a) Studies on the Cationic Polymers According to the Invention

Preparation of the Cationic Polymers

The cationic polymers were dissolved in water and appropriately diluted in the cell culture medium to obtain final concentrations of 10 to $10^{-5}$ mg/ml, used to evaluate after 24, 48 and 72 hours the cytotoxicity on two cell lines: MonoMac-6 and HT29.

MonoMac-6 Cell Line

The human monocyte/macrophage cell line MonoMac-6 was kindly donated by Prof. Mantovani (Humanitas, Italy).

The cells were kept in an incubator at 37° C. with 5% $CO_2$, in RPMI 1640 medium supplemented with 10% foetal calf serum (FCS), 2% L-glutamine, 1% of a penicillin/streptomycin solution, 1% of non-essential amino acids, 1% of 100 mM sodium pyruvate and 1% of oxaloacetic acid.

The cells, which grow in suspension, were maintained in culture by passages performed at a weekly rate, via 1:4 dilutions of the cell culture in a new fresh complete medium.

HT-29 Cell Line

Human colon adenocarcinoma cells HT-29, obtained from the American Type Culture Collection (ATCC Maryland, USA), were maintained in Dulbecco's Modified Eagles medium (DMEM high glucose pH 7.4) supplemented with 10% of foetal calf serum (FCS), 2% of L-glutamine, 1% of a penicillin/streptomycin solution, 1% of non-essential amino acids, 1% of 100 mM sodium pyruvate and 2% of a 1M HEPES solution.

The cells, which grow by adherence, were maintained in culture by performing passages at a weekly rate, seeding 300 000 cells per flask, before treatment with trypsin/EDTA to detach the cells from the monolayer.

Cytotoxicity Assay

The Mono Mac-6 and HT-29 cells plated out in 96-well plates (10 000 cells/well) 24 hours before the experiment, were incubated with the cationic derivatives at various concentrations for 24, 48 and 72 hours.

At the end of the treatment with the test compounds, the cell viability was determined as a function of the production of adenosine triphosphate (ATP) using the kit ATPlite (Perkin-Elmer).

The ATPlite assay is based on the production of luminescence produced following the reaction of ATP, present in the cells, with luciferase and d-luciferin added to the wells before reading. The intensity of the luminescence produced is directly proportional to the concentration of ATP present in the sample and is measured using a luminometer (VICTOR-3 Wallac).

Before performing the luminometer measurement, 50 µl of lysis solution (Triton X-100 0.5% in 0.2N NaOH) in 100 µl of culture medium are added to each well. After 5 minutes of incubation at room temperature and with stirring at 700 rpm, 50 µl of ATPlite kit are added to each well and, after stirring for 5 minutes, the plate is incubated for a further 10 minutes in the dark, before performing the luminescence measurement.

For each derivative, the experiments were performed in duplicate.

The percentage of cell viability was determined by considering the mean of the luminescence values for the treated cells and that for the untreated control cells.

The percentage of cell viability (% CV) for each derivative was expressed as the mean percentage relative to the control, according to the following equation:

$$\text{Viability}(\%) = \frac{\text{Mean luminescence intensity treated cells}}{\text{Mean luminescence intensity untreated cells}} \times 100$$

A compound is considered cytotoxic when the percentage of viability is less than 50%.

TABLE 13 concentration of cationic polymers 0.01 mg/mL

| Polymer No. | MonoMac-6 cell line (in suspension) CV (%) | | | HT29 cell line (adherent) CV (%) | | |
|---|---|---|---|---|---|---|
| | 24 hours | 48 hours | 72 hours | 24 hours | 48 hours | 72 hours |
| 1 | 111 | 97 | 114 | 115 | 78 | 143 |
| 2 | 112 | 61 | 136 | 136 | 107 | 136 |
| 3 | 115 | 208 | 65 | 96 | 131 | 160 |
| 4 | 108 | 217 | 60 | 86 | 118 | 140 |
| 5 | 100 | 176 | 56 | 113 | 107 | 165 |
| 6 | 109 | 132 | 124 | 111 | 138 | 158 |
| 7 | 104 | 80 | 105 | 317 | 92 | 95 |
| 8 | — | — | — | 103 | 61 | 92 |
| 9 | 111 | 143 | 129 | 101 | 120 | 156 |
| 10 | 110 | 144 | 80 | 103 | 143 | 162 |
| 11 | 125 | 110 | 129 | 323 | 101 | 97 |
| 12 | — | — | — | 127 | 72 | 86 |
| 13 | 135 | 121 | 136 | 301 | 95 | 90 |
| 14 | 108 | 71 | 81 | 305 | 92 | 91 |
| 15 | 126 | 115 | 161 | 227 | 92 | 68 |
| 16 | — | — | — | 131 | 83 | 79 |
| 17 | 107 | 137 | 134 | 106 | 123 | 131 |
| 18(*) | 97 | 74 | 109 | 97 | 73 | 105 |
| 50(*) | 105 | 105 | 120 | 97 | 128 | 158 |
| 60(*) | — | — | — | 93 | 114 | 52 |

(*)polymers used for comparison:
18 = DEAE dextran;
50 = unmodified Polglumyt™ glycogen;
60 = polyethyleneimine (PEI).

The results in Table 13 made it possible to demonstrate that the cationic polymers according to the present invention are not cytotoxic at a concentration of 0.01 mg/mL.

TABLE 14 concentration of cationic polymers 0.1 mg/mL

| Polymer No. | MonoMac-6 cell line (in suspension) CV (%) | | | HT29 cell line (adherent) CV (%) | | |
|---|---|---|---|---|---|---|
| | 24 hours | 48 hours | 72 hours | 24 hours | 48 hours | 72 hours |
| 1 | 108 | 86 | 61 | 101 | 96 | 132 |
| 2 | 105 | 152 | 167 | 116 | 110 | 169 |
| 3 | 107 | 182 | 100 | 102 | 127 | 140 |
| 4 | 105 | 165 | 66 | 104 | 122 | 131 |
| 5 | 107 | 182 | 87 | 85 | 147 | 152 |
| 6 | 102 | 151 | 107 | 102 | 110 | 147 |
| 7 | 99 | 54 | 95 | 342 | 81 | 102 |
| 8 | — | — | — | 114 | 149 | 92 |
| 9 | 109 | 182 | 128 | 106 | 118 | 168 |
| 10 | 111 | 152 | 82 | 95 | 156 | 150 |
| 11 | 107 | 82 | 142 | 367 | 105 | 110 |
| 12 | — | — | — | 131 | 91 | 92 |
| 13 | 121 | 123 | 121 | 346 | 92 | 104 |
| 14 | 106 | 81 | 123 | 381 | 114 | 114 |
| 15 | 125 | 109 | 149 | 326 | 113 | 98 |
| 16 | — | — | — | 131 | 159 | 150 |
| 17 | 110 | 124 | 138 | 109 | 120 | 152 |
| 18(*) | 10 | 24 | 16 | 60 | 41 | 45 |
| 50(*) | 105 | 167 | 108 | 97 | 125 | 158 |
| 60(*) | — | — | — | 7 | 6 | 3 |

(*)polymers used for comparison:
18 = DEAE dextran;
50 = Unmodified Polglumyt™ glycogen;
60 = PEI.

The results in Table 14 made it possible to demonstrate that the cationic polymers according to the present invention are not cytotoxic at a concentration of 0.1 mg/mL, unlike DEAE-dextran and PEI.

TABLE 15 concentration of cationic polymers 1.0 mg/mL

| Polymer No. | MonoMac-6 cell line (in suspension) CV (%) | | | HT29 cell line (adherent) CV (%) | | |
|---|---|---|---|---|---|---|
| | 24 hours | 48 hours | 72 hours | 24 hours | 48 hours | 72 hours |
| 1 | 91 | 70 | 76 | 89 | 133 | 109 |
| 2 | 117 | 118 | 153 | 95 | 121 | 145 |
| 3 | 88 | 115 | 32 | 112 | 126 | 133 |
| 4 | 55 | 81 | 50 | 84 | 115 | 108 |
| 5 | 88 | 175 | 45 | 79 | 127 | 159 |
| 6 | 102 | 132 | 89 | 103 | 130 | 149 |
| 7 | 41 | 16 | 12 | 280 | 82 | 84 |
| 8 | — | — | — | 74 | 113 | 86 |
| 9 | 115 | 132 | 103 | 99 | 127 | 163 |
| 10 | 99 | 136 | 55 | 131 | 143 | 155 |
| 11 | 113 | 78 | 136 | 371 | 110 | 111 |
| 12 | — | — | — | 108 | 169 | 135 |
| 13 | 97 | 169 | 63 | 329 | 111 | 99 |
| 14 | 107 | 75 | 131 | 373 | 104 | 112 |
| 15 | 140 | 101 | 105 | 333 | 110 | 100 |
| 16 | — | — | — | 107 | 165 | 125 |
| 17 | 98 | 138 | 138 | 95 | 134 | 128 |
| 18(*) | 13 | 14 | 12 | 49 | 29 | 18 |

TABLE 15-continued concentration of cationic polymers 1.0 mg/mL

| Polymer No. | MonoMac-6 cell line (in suspension) CV (%) | | | HT29 cell line (adherent) CV (%) | | |
|---|---|---|---|---|---|---|
| | 24 hours | 48 hours | 72 hours | 24 hours | 48 hours | 72 hours |
| 50(*) | 98 | 158 | 69 | 98 | 115 | 157 |
| 60(*) | — | — | — | 3 | 6 | 2 |

(*)polymers used for comparison:
18 = DEAE dextran;
50 = Unmodified Polglumyt™ glycogen;
60 = PEI The results in Table 15 made it possible to demonstrate that the cationic polymers according to the present invention, with the exception of polymer 7, are not cytotoxic at a concentration of 1 mg/mL, unlike DEAE-dextran and PEI. Derivative 7 proved to be cytotoxic only on the cell culture in suspension.

TABLE 16 concentration of cationic polymers 10.0 mg/mL

| Polymer No. | HT29 cell line (adherent) CV (%) | | |
|---|---|---|---|
| | 24 hours | 48 hours | 72 hours |
| 1 | 112 | 156 | 164 |
| 2 | 97 | 130 | 177 |
| 3 | 78 | 104 | 128 |
| 4 | 63 | 82 | 71 |
| 5 | 106 | 130 | 174 |
| 6 | 101 | 132 | 170 |
| 7 | 277 | 76 | 83 |
| 8 | 43 | 77 | 56 |
| 9 | 104 | 135 | 165 |
| 10 | 52 | 120 | 172 |
| 11 | 362 | 116 | 108 |
| 12 | 93 | 166 | 115 |
| 13 | 379 | 116 | 113 |
| 14 | 361 | 123 | 108 |
| 15 | 308 | 110 | 92 |
| 16 | 79 | 146 | 95 |
| 17 | 97 | 129 | 176 |
| 18(*) | 49 | 27 | 28 |
| 50(*) | 89 | 135 | 151 |
| 60(*) | 2 | 2 | 1 |

(*)polymers used for comparison: 18 = DEAE dextran; 50 = Unmodified Polglumyt™ glycogen; 60 = PEI.

The results in Table 16 made it possible to demonstrate that the cationic polymers according to the present invention are not cytotoxic at a concentration of 10 mg/mL, unlike DEAE-dextran and PEI.

(b) Studies on Fluorescent Derivatives of the Cationic Polymers According to the Present Invention The cytotoxicity studies were also performed using fluorescent derivatives of the cationic polymers according to the present invention, for the purposes of determining the highest non-cytotoxic concentration at which to perform the cell uptake studies.

The fluorescent derivatives of the cationic polymers according to the present invention were synthesized as follows.

500 mg of one of the cationic polymers according to the present invention were dissolved, in the absence of light, in 10 mL of distilled water in a two-necked round-bottomed flask equipped with a magnetic stirrer. 2 mL of 1N NaOH were added and the mixture was stirred at room temperature for 1.5 hours. Next, 36 mg of fluorescein isothiocyanate (FITC) dissolved in about 0.3 mL of DMSO were added. The mixture was stirred at room temperature overnight.

The next day, 20 mL of acetone were poured into the reaction flask and, after stirring for about 30 minutes, the polymer was allowed to deposit. The supernatant was discarded and the precipitate was washed twice with about 20 mL of acetone.

The precipitate was then dissolved in about 10 mL of distilled water and the solution was subjected to dialysis in regenerated cellulose tubes (cut-off 15,000) against distilled water, in the absence of light. Once the dialysis was complete, the solution was filtered through a 0.45 µm filter and freeze-dried.

These studies were performed on HT29 adherent cells, prepared as described previously.

The results are collated in Table 17 below, in which the fluorescent derivatives of the cationic polymers according to the present invention have been indicated by the same numbering as in Table 2, with the addition of an "f".

TABLE 17

| No. | Conc. 0.01 mg/mL | | | Conc. 0.1 mg/mL | | | Conc. 1 mg/mL | | | Conc. 10 mg/mL | | |
|---|---|---|---|---|---|---|---|---|---|---|---|---|
| | 24 h | 48 h | 72 h | 24 h | 48 h | 72 h | 24 h | 48 h | 72 h | 24 h | 48 h | 72 h |
| 1f | 119 | 142 | 115 | 111 | 116 | 125 | 106 | 108 | 131 | 97 | 116 | 125 |
| 2f | 102 | 159 | 133 | 101 | 112 | 83 | 100 | 115 | 119 | 77 | 100 | 89 |
| 3f | 92 | 123 | 102 | 71 | 84 | 107 | 75 | 90 | 105 | 53 | 74 | 61 |
| 4f | 69 | 86 | 94 | 79 | 59 | 78 | 56 | 31 | 71 | 36 | 32 | 34 |
| 5f | 114 | 100 | 133 | 98 | 94 | 134 | 107 | 106 | 116 | 105 | 78 | 106 |
| 6f | 105 | 90 | 118 | 101 | 154 | 91 | 98 | 92 | 116 | 98 | 72 | 75 |
| 7f | 94 | 128 | 114 | 102 | 120 | 112 | 73 | 72 | 88 | 59 | 52 | 40 |
| 8f | 103 | 61 | 92 | 114 | 149 | 92 | 74 | 113 | 86 | 43 | 77 | 56 |
| 9f | 92 | 67 | 69 | 89 | 83 | 37 | 72 | 71 | 36 | 77 | 57 | 33 |
| 10f | 95 | 151 | 114 | 93 | 119 | 82 | 94 | 120 | 75 | 56 | 79 | 35 |
| 11f | 111 | 105 | 147 | 100 | 90 | 144 | 75 | 75 | 123 | 81 | 50 | 94 |

TABLE 17-continued

| | Conc. 0.01 mg/mL | | | Conc. 0.1 mg/mL | | | Conc. 1 mg/mL | | | Conc. 10 mg/mL | | |
|---|---|---|---|---|---|---|---|---|---|---|---|---|
| No. | 24 h | 48 h | 72 h | 24 h | 48 h | 72 h | 24 h | 48 h | 72 h | 24 h | 48 h | 72 h |
| 12f | 127 | 72 | 86 | 131 | 91 | 92 | 108 | 169 | 135 | 93 | 166 | 115 |
| 13f | 93 | 100 | 96 | 97 | 122 | 75 | 110 | 90 | 104 | 63 | 70 | 47 |
| 14f | 102 | 94 | 103 | 102 | 119 | 137 | 103 | 78 | 156 | 74 | 65 | 101 |
| 15f | 93 | 81 | 137 | 81 | 105 | 150 | 77 | 87 | 122 | 69 | 59 | 88 |
| 16f | 131 | 83 | 79 | 131 | 159 | 150 | 107 | 165 | 125 | 79 | 146 | 95 |
| 18f(*) | 15 | 10 | 11 | 20 | 7 | 13 | 17 | 12 | 6 | 20 | 8 | 10 |

(*)comparative:
18f = fluorescent derivate of DEAE-dextran

From the results obtained, it was observed that the highest concentration at which all the fluorescent derivatives of the cationic polymers according to the present invention were non-cytotoxic, over a 24-hour period, was 1 mg/ml. In contrast, the fluorescent derivative of DEAE-dextran was highly cytotoxic at all the concentrations analysed.

Example 7

Cell Uptake Studies

The cell uptake studies were performed at 2, 6 and 24 hours, using the fluorescent derivatives of the cationic polymers of the present invention (1f-16f) and DEAE-dextran hydrochloride, at a concentration of 1 mg/mL, i.e. the highest concentration analysed in the cytotoxicity studies at which the fluorescent derivatives 1f-16f proved to be non-cytotoxic over a 24-hour period.

The studies were performed using HT29 adherent cells, treated according to the following procedure.

HT-29 cells, plated out the day before the experiment at a density of 20,000 cells/well, were incubated with the respective fluorescent derivatives at a concentration of 1 mg/ml for 2, 6 and 24 hours. At the end of each incubation period, the medium was removed from the wells and the cells were washed with a standard pH 7.4 phosphate-buffered saline (PBS) three times.

Next, the cells were treated with 200 µl of lysis solution (Triton X-100 0.5% in 0.2N NaOH) and the fluorescence was measured by fluorimetry ($\lambda$ exc. 485 nm; $\lambda$ em. 535 nm).

For each compound and for each time, the mean fluorescence of two replicates was calculated, the values of which are given in Table 18.

TABLE 18

| | Fluorescence intensity | | |
|---|---|---|---|
| Polymer No. | 2 hours | 6 hours | 24 hours |
| 1f | 1696 | 1372 | 744 |
| 2f | 5567 | 6327 | 7217 |
| 3f | 17531 | 24101 | 30573 |
| 4f | 70210 | 63668 | 120662 |
| 5f | 4845 | 4365 | 3274 |
| 6f | 6842 | 8306 | 7651 |
| 7f | 26268 | 36314 | 52612 |
| 8f | 19638 | 34463 | 58024 |
| 9f | 2386 | 2991 | 2487 |
| 10f | 3122 | 4318 | 3177 |
| 11f | 10866 | 12491 | 8906 |
| 12f | 14020 | 21569 | 37090 |
| 13f | 937 | 1736 | 1008 |
| 14f | 4599 | 7724 | 4190 |

TABLE 18-continued

| | Fluorescence intensity | | |
|---|---|---|---|
| Polymer No. | 2 hours | 6 hours | 24 hours |
| 15f | 13319 | 22623 | 30889 |
| 16f | 23560 | 48650 | 56919 |
| 18f(*) | 15227 | 13689 | 12626 |
| control | 833 | 1152 | 349 |

The effective amount of cell uptake for the fluorescent derivatives was calculated by constructing a calibration curve for each fluorescent derivative in the cell lysis solvent (Triton X-100 at 0.5% in 0.2N NaOH).

From the calibration curves and from the fluorescence intensities observed, the amount in mg/mL of cell uptake was calculated, as described in Table 19.

TABLE 19

| | Concentration mg/mL | | |
|---|---|---|---|
| Polymer No. | 2 h | 6 h | 24 h |
| 2f | 0.006 | 0.006 | 0.007 |
| 3f | 0.008 | 0.014 | 0.021 |
| 4f | 0.019 | 0.017 | 0.036 |
| 5f | 0.002 | 0.001 | 0.000 |
| 6f | 0.002 | 0.003 | 0.002 |
| 7f | 0.026 | 0.036 | 0.053 |
| 8f | 0.005 | 0.012 | 0.024 |
| 11f | 0.002 | 0.003 | 0.001 |
| 12f | 0.004 | 0.008 | 0.016 |
| 14f | 0.006 | 0.009 | 0.005 |
| 15f | 0.004 | 0.014 | 0.022 |
| 16f | 0.008 | 0.020 | 0.025 |
| 18f(*) | 0.002 | 0.002 | 0.001 |

(*)fluorescent DEAE-dextran

The results obtained showed the degree of cell uptake of the cationic polymers according to the invention relative to DEAE-dextran.

Moreover, it was noted that the degree of derivatization had a directly proportional influence on the cell uptake.

Example 8

Evaluation of the Buffer Capacity

The buffer capacity was evaluated to check that the cationic polymers according to the present invention would have characteristics such that they would also induce the "proton-sponge" effect, which is considered necessary to enable the release of the polymer-nucleic acid complex from endosomes, following cellular absorption.

The cationic polymers according to the invention (DEAE-glycogen) and DEAE-dextran were titrated upon transformation into the hydrochloride (as described in Example 2) with NaOH, the titration being monitored by pH variation.

100 mg of polymer hydrochloride were dissolved in 100 mL of distilled water, the solution being stirred overnight at room temperature. The next day, the solution was titrated with 0.01 N NaOH, the addition of titrant being performed with a dosimeter and the titration being monitored with a pH-meter.

The titration studies, performed on the cationic derivatives according to the present invention, made it possible to identify a $pK_a$ distribution below and at about the physiological pH in a range of between about 4.5-8, which gives the cationic polymers of the invention a high buffer capacity.

The $pK_a$ values at about the physiological pH were useful for giving the cationic polymers of the invention the positive charge necessary for the complexation of nucleic acids.

The $pK_a$ values below the physiological pH were useful for ensuring the release of complexes from the endosomes into the cytoplasm (via the "proton sponge" effect).

Figure 9:
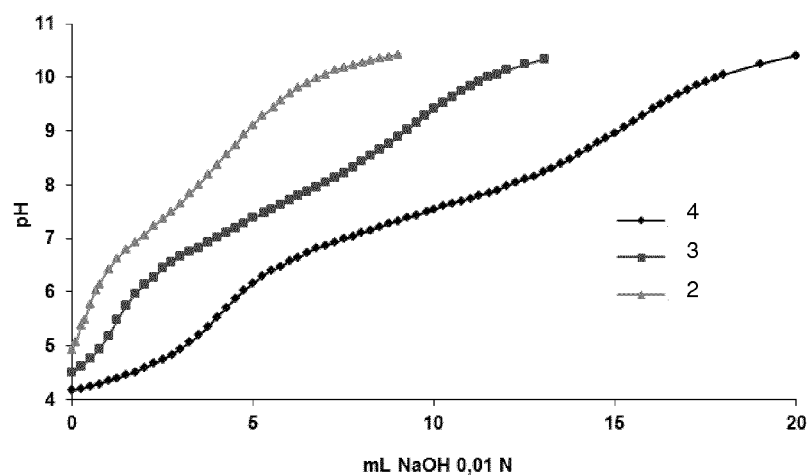
FIG. 9 shows the titration curve for polymers 2, 3 and 4 according to the invention, obtained as described in Example 8.

FIG. 9 shows the titration curves for the cationic polymers 2, 3 and 4 (DEAE-glycogen, according to the present invention) for comparative purposes. It may be noted that within the same class of derivatives, the buffer capacity increased as the degree of derivatization increased.

Figure 10:
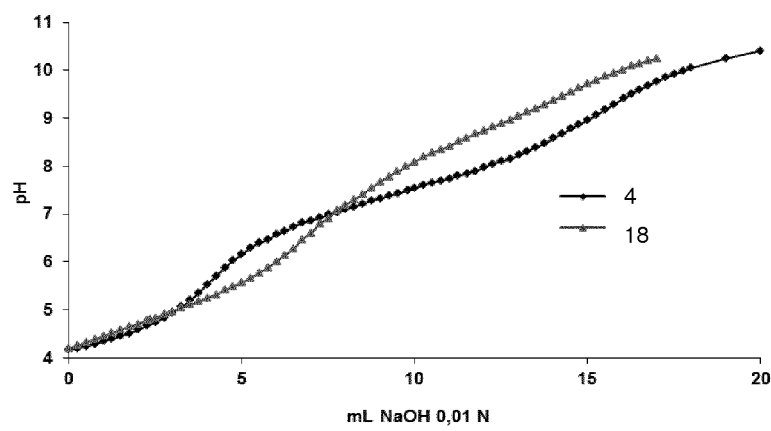
FIG. 10 shows the titration curve for polymers 4 (according to the invention) and 18 (comparative) obtained as described in Example 8.

In addition, it was observed that polymer 4 (DEAE-glycogen) and product 18 (DEAE-dextran) had a similar degree of derivatization and comparable buffer capacity, as shown in FIG. 10.

Example 9

Rheological Measurements

The rheological studies were performed on the cationic derivatives 1-16 according to the present invention (DEAE-, DMAP-, DMAE-, 2-OH-PTMA-glycogen) and on DEAE-dextran hydrochloride, at a concentration of 1% in PBS.

The measurements were performed using a Bohlin Gemini 150 rotary rheometer piloted by the Bohlin R6 40.5.32 software, equipped with cone-plate geometry 2°/55 mm, thermostatically maintained with a Peltier Bohlin instrument at 25° C. and performed in "controlled stress" mode in a shear stress range of 1-5 Pa.

All the samples analysed showed a very low viscosity value, of mPa*s order. This characteristic made it possible to use the cationic derivatives according to the present invention also by injection.

By way of example, Table 20 reports the viscosity values of the various derivatives at a single stress value (2.5 Pa).

TABLE 20

| Polymer No. | Viscosity at 2.5 Pa (Pa · s) |
|---|---|
| 1 | $1.97 \times 10^{-3}$ |
| 2 | $1.91 \times 10^{-3}$ |
| 3 | $1.91 \times 10^{-3}$ |
| 4 | $1.95 \times 10^{-3}$ |
| 5 | $1.97 \times 10^{-3}$ |
| 6 | $1.95 \times 10^{-3}$ |
| 7 | $1.91 \times 10^{-3}$ |
| 8 | $1.96 \times 10^{-3}$ |
| 9 | $1.87 \times 10^{-3}$ |
| 10 | $1.96 \times 10^{-3}$ |
| 11 | $1.92 \times 10^{-3}$ |
| 12 | $1.91 \times 10^{-3}$ |
| 13 | $1.93 \times 10^{-3}$ |
| 14 | $1.94 \times 10^{-3}$ |

TABLE 20-continued

| Polymer No. | Viscosity at 2.5 Pa (Pa · s) |
|---|---|
| 15 | $1.93 \times 10^{-3}$ |
| 16 | $1.98 \times 10^{-3}$ |
| 18(*) | $2.36 \times 10^{-3}$ |

(*)comparative: DEAE-dextran

Example 10

Cytotoxicity Studies with Cationic Derivatives of Glycogen Complexed with Anionic Molecules HT-29 cells were plated out the day before the experiment at a density of 10,000 cells/well in a volume of 100 µl of DMEM medium containing 10% serum.

On the day of the experiment, the medium was removed from the wells and 150 µl of DMEM medium containing 2.5% serum were added. 50 µl of complexes formed from a cationic polymer according to the present invention and fluorescent siRNA were then added. The complexes formed from a cationic polymer according to the present invention and fluorescent siRNA were prepared according to the following procedure.

Four solutions were prepared, each containing 6.283 mg of cationic polymer 3, 7, 11 and 15 in 40 ml of RNase-free PBS. To 142.86 µL of each of the solutions were added 6.6 µL of a solution of siRNA in RNase-free PBS (concentration of 20 µM) and, after a few minutes, each was diluted with 350.54 µL of RNase-free PBS. The final concentration of siRNA in the solutions was 264 nM, equivalent to 10% by weight of siRNA relative to the weight of the polymer.

The solutions thus obtained were stirred for about 30 seconds, incubated at room temperature for 10 minutes, stirred again for 30 seconds and left to stand for 5 minutes. Before performing the experiment, the solutions were stirred again for 30 seconds.

The solutions (50 µl) of the cationic polymers 3, 7, 11 and 15 in 40 ml of RNase-free PBS, to which no siRNA was added, were used as a first comparison.

A complex between siRNA and the transfection reagent Lipofectamine® 2000, prepared according to the procedure described by the manufacturer Life-Technologies™ for the transfection of siRNA and containing the same amount of siRNA used in the complexes with the polymers, was used as a second comparison.

The transfection reagent Lipofectamine® 2000 to which no siRNA was added was used as a third comparison.

The complexes and all the comparative materials prepared as described above were placed in contact with the cells.

The cells were incubated for 4 and 24 hours at 37° C., after which the supernatant was removed and 100 µl of medium containing 2.5% serum were added.

At the end of the treatment with the test compounds, the cell viability was determined as a function of the production of adenosine triphosphate (ATP), using the kit ATPlite (Perkin-Elmer), as described for Example 6 hereinabove.

The results, determined as described in Example 6, are expressed as a percentage of live cells, in Table 21 below.

TABLE 21

| Polymer No. | Cell viability CV (%) | |
| --- | --- | --- |
| | 4 h | 24 h |
| 3 + siRNA | 58 | 100 |
| 7 + siRNA | 89 | 85 |
| 11 + siRNA | 91 | 70 |
| 15 + siRNA | 101 | 59 |
| First comparison | | |
| 3 | 92 | 105 |
| 7 | 90 | 99 |
| 11 | 85 | 85 |
| 15 | 86 | 72 |
| Second comparison | | |
| Lipofectamine ® 2000 + siRNA | 130 | 110 |
| Third comparison | | |
| Lipofectamine ® 2000 | 110 | 108 |

The results obtained demonstrated that the complexes obtained between the cationic polymers according to the present invention and siRNA are not cytotoxic.

Consequently, the cationic polymers 3, 7, 11 and 15 were used in the following cell uptake study.

Example 11

Cell Uptake Studies with Cationic Derivatives of Glycogen Complexed with Fluorescent Anionic Molecules The studies were performed in a manner similar to that described in Example 7 hereinabove, using HT29 adherent cells.

HT-29 cells were plated out the day before the experiment at a density of 20,000 cells/well in a volume of 100 μl of DMEM medium containing 10% serum.

On the day of the experiment, the medium was removed from the wells and 150 μl of DMEM medium containing 2.5% serum were added. 50 μl of the complexes formed from a cationic polymer according to the present invention and fluorescent siRNA were then added.

The complexes formed from a cationic polymer according to the present invention and fluorescent siRNA were prepared according to the following procedure.

Four solutions were prepared, each containing 6.2832 mg of cationic polymer 3, 7, 11 and 15 in 40 ml of RNase-free PBS. To 142.86 μL of each of these solutions were added 6.6 μL of a solution of siRNA in RNase-free PBS (concentration of 20 μM) and, after a few minutes, each was diluted with 350.54 μL of RNase-free PBS. The siRNA was labelled with a fluorescent compound Alexa-488. The final concentration of siRNA was 264 nM, equivalent to 10% by weight of siRNA relative to the weight of the polymer.

The solutions thus obtained were stirred for about 30 seconds, incubated at room temperature for 10 minutes, stirred for a further 30 seconds and left to stand for 5 minutes. Before performing the experiment, the solutions were stirred again for a further 30 seconds.

A complex between siRNA and the transfection reagent Lipofectamine® 2000, prepared according to the procedure described by the manufacturer Life-Technologies™ for the transfection of siRNA and containing the same amount of siRNA used in the complexes with the polymers, was used as a first comparison.

The fluorescence of siRNA alone was measured as a subsequent comparison.

The complexes and all the comparative materials prepared as described above were placed in contact with the cells.

The cells were incubated for 4 hours at 37° C. and, after discarding the supernatant, the cells were washed twice with 200 μl of PBS.

Next, the cells were treated with 200 μl of lysis solution (Triton X-100 0.5% in 0.2N NaOH) for 5 minutes, at room temperature with stirring.

The fluorescence emitted by the siRNA labelled with Alexa-488, which was taken up, was measured by fluorimeter (λ exc. 485 nm; λ em. 535 nm), after the complexes between the polymers and siRNA had been maintained in contact with the cells for 4 hours.

For each polymer, the experiment was performed in triplicate and the mean fluorescence intensity was then calculated. From this value was subtracted the mean value of the fluorescence intensity calculated for the culture medium alone, which was equal to 1366, giving the final fluorescence intensity.

The same procedure was followed for the first comparison (Lipofectamine® 2000+siRNA) for which the mean fluorescence intensity value for the culture medium alone was equal to 1328.

The results are collated in Table 22.

TABLE 22

| Polymer No. | Fluorescence intensity | | | | |
| --- | --- | --- | --- | --- | --- |
| | Recorded | | | Mean | Final |
| 3 | 2533 | 2504 | 2642 | 2560 | 1194 |
| 7 | 2721 | 2973 | 3066 | 2920 | 1554 |
| 11 | 1906 | 1801 | 1856 | 1854 | 489 |
| 15 | 2493 | 2927 | 2851 | 2757 | 1391 |
| Lipofectamine ® 2000 + siRNA | 1811 | 1820 | 1845 | 1825 | 498 |
| siRNA | 1334 | 1351 | 1267 | 1317 | — |

The results obtained demonstrated that the cationic polymers according to the invention are capable of inducing the uptake of siRNA into the cell membrane. In addition, the cationic polymers according to the invention made it possible to take up a larger amount of siRNA than the complex used as comparison comprising Lipofectamine® 2000.

The invention claimed is:
1. A glycogen-based cationic polymer, which is a polymer comprising at least one repeating unit selected from the group consisting of (a) and (b):

(a)

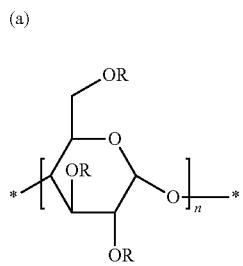

in which
groups R, which may be identical or different, are a hydrogen atom, a carboxymethyl group, optionally in salt form with a pharmaceutically acceptable organic or inorganic base, or a group selected from the group consisting of NH$_2$—(C$_1$-C$_6$)alkyl, [N,N-di(C$_1$-C$_6$)alkylamino]-(C$_1$-C$_6$)alkyl, NH$_2$—{[(C$_1$-C$_6$)alkyl-di(C$_1$-C$_6$)alkylammonio]}-(C$_1$-C$_6$) alkyl, {[N,N-di(C$_1$-C$_6$)alkylamino]-(C$_1$-C$_6$)alkyl-di(C$_1$-C$_6$)alkylammonio}-(C$_1$-C$_6$)alkyl, NH$_2$—[(C$_1$-C$_6$)alkylamino]-(C$_1$-C$_6$)alkyl, {[N,N-di(C$_1$-C$_6$)alkylamino]-(C$_1$-C$_6$)alkylamino}-(C$_1$-C$_6$)alkyl, [tri(C$_1$-C$_6$)alkylammonio]-(C$_1$-C$_6$)alkyl, and azocyclyl-(C$_1$-C$_6$)alkyl, in which said (C$_1$-C$_6$)alkyl chains, which may be identical or different, are optionally substituted with one or more hydroxyl groups, and n is an integer greater than or equal to 1; and (b)

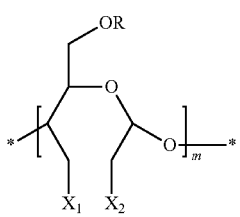

(b)

in which

R$_1$ is a hydrogen atom, a carboxymethyl group, optionally in salt form with a pharmaceutically acceptable organic or inorganic base, or a group comprising nitrogen selected from the group consisting of: NH$_2$—(C$_1$-C$_6$) alkyl, [N,N-di(C$_1$-C$_6$)-alkylamino]-(C$_1$-C$_6$)alkyl, NH$_2$—[(C$_1$-C$_6$)alkyl-di(C$_1$-C$_6$)alkylammonio]-(C$_1$-C$_6$)-alkyl, {[N,N-di(C$_1$-C$_6$)alkylamino]-(C$_1$-C$_6$)alkyl-di(C$_1$-C$_6$)alkylammonio}-(C$_1$-C$_6$)alkyl, NH$_2$—[(C$_1$-C$_6$)alkylamino]-(C$_1$-C$_6$)alkyl, {[N,N-di(C$_1$-C$_6$)alkylamino]-(C$_1$-C$_6$)alkylamino}-(C$_1$-C$_6$)alkyl, and [tri(C$_1$-C$_6$)alkylammonio]-(C$_1$-C$_6$)-alkyl, in which said (C$_1$-C$_6$)alkyl chains, which may be identical or different, are optionally substituted with one or more hydroxyl groups;

X$_1$ and X$_2$, which may be identical or different, are a group —OH or a group —NHR$_2$, in which R$_2$ is selected from the group consisting of: a hydrogen atom, (C$_1$-C$_6$)alkyl, and H—[NH—(C$_1$-C$_6$)alkyl]$_p$-, where p is an integer greater than or equal to 1 and said groups (C$_1$-C$_6$)alkyl may be identical or different; and m is an integer greater than or equal to 1;

with the provisos that at least one group from among R, R$_1$, X$_1$ and X$_2$ is a group containing nitrogen, and the glycogen-based cationic polymer is different from a product obtained by reacting glycogen with N-(3-chloro-2-hydroxypropyl)-trimethyl ammonium chloride.

2. The glycogen-based cationic polymer of claim 1, which comprises at least one repeating unit (a), wherein the groups R, which may be identical or different, are a hydrogen atom, a carboxymethyl group, optionally in salt form with a pharmaceutically acceptable organic or inorganic base or a group selected from the group consisting of: [N,N-di(C$_1$-C$_3$)alkylamino]-(C$_1$-C$_3$)alkyl, {[N,N-di(C$_1$-C$_3$)alkylamino]-(C$_1$-C$_3$)alkyl-di(C$_1$-C$_3$)alkylammonio}-(C$_1$-C$_3$) alkyl, {[N,N-di(C$_1$-C$_3$)alkylamino]-(C$_1$-C$_3$)alkylamino}-(C$_1$-C$_3$)alkyl, [tri(C$_1$-C$_3$)alkylammonio]-(C$_1$-C$_3$)alkyl, and azocyclyl-(C$_1$-C$_3$)alkyl, in which said (C$_1$-C$_3$)alkyl chains, which may be identical or different, are optionally substituted with a hydroxyl group.

3. The glycogen-based cationic polymer of claim 2, wherein the groups R, which may be identical or different, are a hydrogen atom, a carboxymethyl group, optionally in salt form with a pharmaceutically acceptable organic or inorganic base or a group selected from the group consisting of: N,N-dimethylamino-ethyl, N,N-dimethylamino-propyl, N,N-diethylamino-ethyl, [(N,N-dimethyl-aminoethyl)dimethylammonio]ethyl, [(N,N-dimethylamino-propyl)-dimethylammonio]propyl, [(N,N-diethylaminoethyl)diethylammonio]-ethyl, [trimethylammonio]-2-hydroxypropyl, piperidyl-N-ethyl and morpholinyl-N-ethyl.

4. The glycogen-based cationic polymer of claim 1, which comprises at least one repeating unit (b), wherein R$_1$ is a hydrogen atom, a carboxymethyl group, optionally in salt form with a pharmaceutically acceptable organic or inorganic base, or a group selected from the group consisting of: [N,N-di(C$_1$-C$_3$)alkylamino]-(C$_1$-C$_3$)alkyl], {[N,N-di(C$_1$-C$_3$)alkylamino]-(C$_1$-C$_3$)-alkyldi(C$_1$-C$_3$)alkylammonio}-(C$_1$-C$_3$)alkyl, {[N,N-di(C$_1$-C$_3$)alkyl-amino]-(C$_1$-C$_3$) alkylamino}-(C$_1$-C$_3$)alkyl and [tri(C$_1$-C$_3$)alkylammonio]-(C$_1$-C$_3$)alkyl, in which said (C$_1$-C$_3$)alkyl chains, which may be identical or different, are optionally substituted with a hydroxyl group.

5. The glycogen-based cationic polymer of claim 4, wherein R$_1$ is a hydrogen atom or a carboxymethyl group.

6. The glycogen-based cationic polymer of claim 1, which comprises at least one repeating unit (b), wherein X$_1$ and X$_2$, which may be identical or different, are a group —NHR$_2$, in which R$_2$ is a hydrogen atom or H—[NH—(C$_1$-C$_4$)alkyl]$_p$-, where p is an integer greater than or equal to 1 and said (C$_1$-C$_4$)alkyl groups may be identical or different.

7. The glycogen-based cationic polymer of claim 6, wherein the group H—[NH—(C$_1$-C$_4$)alkyl]$_p$- is a polyethyleneimine, with a molecular weight of from 50 to 3,000 daltons, spermine (H$_2$N(CH$_2$)$_3$NH(CH$_2$)$_4$NH(CH$_2$)$_3$NH$_2$), or spermidine (H$_2$N(CH$_2$)$_4$NH(CH$_2$)$_4$NH$_2$).

8. The glycogen-based cationic polymer of claim 1, wherein the repeating units (a) and (b) comprise:
at least one group that is ionizable at physiological pH, selected from the group consisting of: NH$_2$—(C$_1$-C$_6$) alkyl, [N,N-di(C$_1$-C$_6$)alkylamino]-(C$_1$-C$_6$)alkyl, NH$_2$—(C$_1$-C$_6$)alkylamino}-(C$_1$-C$_6$)alkyl, {[N,N-di(C$_1$-C$_6$)alkylamino]-(C$_1$-C$_6$)alkylamino}-(C$_1$-C$_6$)alkyl and azocyclyl-(C$_1$-C$_6$)alkyl; and
at least one group that is ionizable at a pH below physiological pH, selected from the group consisting of: NH$_2$—{[(C$_1$-C$_3$)alkyl]-di(C$_1$-C$_6$)alkylammonio}-(C$_1$-C$_6$)alkyl and {[N,N-di(C$_1$-C$_3$)alkylamino]-(C$_1$-C$_6$) alkyl-di(C$_1$-C$_6$)alkylammonio}-(C$_1$-C$_6$)alkyl.

9. A complex, comprising a glycogen-based cationic polymer of claim 1 and an anionic compound.

10. The complex of claim 9, comprising between 5% and 60% by weight of the anionic compound relative to a weight of the glycogen-based cationic polymer.

11. The complex of claim 9, comprising between 10% and 50% by weight of the anionic compound relative to a weight of the glycogen-based cationic polymer.

12. A pharmaceutical composition comprising:
(A) a complex between (1) a glycogen-based cationic polymer, which is a polymer comprising at least one repeating unit chosen from the group consisting of (a) and (b):

(a)

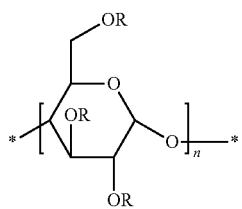

(a)

in which groups R, which may be identical or different, are a hydrogen atom, a carboxymethyl group, optionally in salt form with a pharmaceutically acceptable organic or inorganic base, or a group selected from the group consisting of $NH_2$—$(C_1$-$C_6)$alkyl, [N,N-di($C_1$-$C_6$)alkylamino]-($C_1$-$C_6$)alkyl, $NH_2$—{[($C_1$-$C_6$)alkyl-di($C_1$-$C_6$)alkylammonio]}-($C_1$-$C_6$)alkyl, {[N,N-di($C_1$-$C_6$)alkylamino]-($C_1$-$C_6$)alkyl-di($C_1$-$C_6$)alkyl-ammonio}-($C_1$-$C_6$)alkyl, $NH_2$—[($C_1$-$C_6$)alkylamino]-($C_1$-$C_6$)alkyl, {[N,N-di-($C_1$-$C_6$)alkylamino]-($C_1$-$C_6$)alkylamino}-($C_1$-$C_6$)alkyl, [tri($C_1$-$C_6$)alkyl-ammonio]-($C_1$-$C_6$) alkyl, and azocyclyl-($C_1$-$C_6$)alkyl, in which said ($C_1$-$C_6$)alkyl chains, which may be identical or different, are optionally substituted with one or more hydroxyl groups, and n is an integer greater than or equal to 1; and (b)

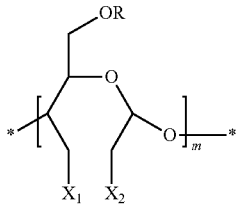

(b)

in which $R_1$ is a hydrogen atom, a carboxymethyl group, optionally in salt form with a pharmaceutically acceptable organic or inorganic base, or a group selected from the group consisting of: $NH_2$—($C_1$-$C_6$)alkyl, [N,N-di($C_1$-$C_6$)alkylamino]-($C_1$-$C_6$)alkyl, $NH_2$—[($C_1$-$C_6$)alkyl-di($C_1$-$C_6$)alkylammonio]-($C_1$-$C_6$)alkyl, {[N,N-di($C_1$-$C_6$)alkylamino]-($C_1$-$C_6$)alkyl-di($C_1$-$C_6$)alkylammonio}-($C_1$-$C_6$)alkyl, $NH_2$—[($C_1$-$C_6$)alkylamino]-($C_1$-$C_6$)alkyl, {[N,N-di($C_1$-$C_6$)alkylamino]-($C_1$-$C_6$)alkylamino}-($C_1$-$C_6$)alkyl, and [tri($C_1$-$C_6$)alkylammonio]-($C_1$-$C_6$)-alkyl, in which said ($C_1$-$C_6$) alkyl chains, which may be identical or different, are optionally substituted with one or more hydroxyl groups;

$X_1$ and $X_2$, which may be identical or different, are a group —OH or a group —$NHR_2$, in which $R_2$ is selected from the group consisting of: a hydrogen atom, ($C_1$-$C_6$)alkyl, and H—[NH—($C_1$-$C_6$)alkyl]$_p$-, where p is an integer greater than or equal to 1 and the groups ($C_1$-$C_6$)alkyl may be identical or different; and m is an integer greater than or equal to 1;

at least one group from among R, $R_1$, $X_1$ and $X_2$ is a group comprising nitrogen, and (2) an anionic compound; and (B) at least one pharmaceutically acceptable excipient.

13. The pharmaceutical composition of claim 12, wherein the anionic compound is a nucleic acid.

14. The pharmaceutical composition of claim 12, which is suitable for injectable use.

15. The glycogen-based cationic polymer of claim 1, comprising at least one repeating unit (a).

16. The glycogen-based cationic polymer of claim 1, comprising at least one repeating unit (b).

17. The glycogen-based cationic polymer of claim 1, comprising at least one repeating unit (a) and at least one repeating unit (b).

* * * * *